US010800819B2

(12) United States Patent
Armstrong et al.

(10) Patent No.: US 10,800,819 B2
(45) **Date of Patent: *Oct. 13, 2020**

(54) VEGETATIVE INSECTICIDAL PROTEINS USEFUL FOR CONTROL OF INSECT PESTS

(71) Applicant: Dow AgroSciences LLC, Indianapolis, IN (US)

(72) Inventors: Janna Mai Armstrong, Indianapolis, IN (US); Audrey Jane Etter, Indianapolis, IN (US); Meghan L. Frey, Greenwood, IN (US); Premchand Gandra, Zionsville, IN (US); Ted Letherer, Indianapolis, IN (US); Gaofeng Lin, Zionsville, IN (US); Krishna M. Madduri, Indianapolis, IN (US); Haley Mowery, Indianapolis, IN (US); Kenneth E. Narva, Zionsville, IN (US); Joel J. Sheets, San Luis Obispo, CA (US); Sek Yee Tan, Carmel, IN (US)

(73) Assignee: DOW AGROSCIENCES LLC

( * ) Notice: Subject to any disclaimer, the term of this patent is extended or adjusted under 35 U.S.C. 154(b) by 0 days.

This patent is subject to a terminal disclaimer.

(21) Appl. No.: 15/824,372

(22) Filed: Nov. 28, 2017

(65) Prior Publication Data

US 2018/0086795 A1 Mar. 29, 2018

Related U.S. Application Data

(62) Division of application No. 14/740,326, filed on Jun. 16, 2015, now Pat. No. 9,879,055.

(60) Provisional application No. 62/014,916, filed on Jun. 20, 2014.

(51) Int. Cl.
| | |
|---|---|
| *C12N 15/82* | (2006.01) |
| *C07K 14/32* | (2006.01) |
| *A01N 37/46* | (2006.01) |
| *C07K 14/325* | (2006.01) |
| *A01N 63/10* | (2020.01) |

(52) U.S. Cl.
CPC .............. *C07K 14/32* (2013.01); *A01N 37/46* (2013.01); *A01N 63/10* (2020.01); *C07K 14/325* (2013.01); *C12N 15/8286* (2013.01); *Y02A 40/162* (2018.01)

(58) Field of Classification Search
None
See application file for complete search history.

(56) References Cited

U.S. PATENT DOCUMENTS

| | | | | |
|---|---|---|---|---|
| 7,378,493 | B2 | 5/2008 | Shen et al. | |
| 8,569,583 | B2 | 10/2013 | Donovan et al. | |
| 8,916,687 | B2 | 12/2014 | Zhang et al. | |
| 9,879,055 | B2 * | 1/2018 | Armstrong ......... | C12N 15/8286 |
| 2008/0104730 | A1 | 5/2008 | Wu et al. | |
| 2009/0241217 | A9 * | 9/2009 | Wu .................... | C12N 15/8273 800/278 |

FOREIGN PATENT DOCUMENTS

| | | | |
|---|---|---|---|
| EP | 3235373 | A1 | 10/2017 |
| WO | 2010/120452 | A1 | 10/2010 |
| WO | 2010/147879 | A1 | 12/2010 |
| WO | 2013/116758 | A1 | 8/2013 |
| WO | WO 2013/134523 | | 9/2013 |
| WO | 2014/004458 | A3 | 1/2014 |

OTHER PUBLICATIONS

International Search Report for Application No. PCT/US15/35914, filed Jun. 16, 2015, dated Dec. 1, 2015.
Hernandez-Rodriguez, C.S.; et al.: "Screening and identification of vip genes in Bacillus thuringiensis strains", Journal of Applied Microbiology, 2009, vol. 107, pp. 219-225.

Lira, Justin; et al.: "Insecticidal Activity of Bacillus thuringiensis Cry1Bh1 against Ostrinia nubilalis (Hübner) (Lepidoptera: Crambidae) and Other Lepidopteran Pests", Applied and Environmental Microbiology, Dec. 2013, vol. 79, No. 24, pp. 7590-7597.

Abdelkefi-Mesrati, L et al. 2011, "Study of the Bacillus thuringiensis Vip3Aa16 histopathological effects and determination of its binding proteins in the midgut of Spodoptera littoralis," J. Inv. Pathol. 106:250-254.

Crickmore N, Zeigler D R, Feitelson J, Schnepf E, Van Rie J, Lereclus D, Baum J, Dean DH. (1998) Revision of the Nomenclature for the Bacillus thuringiensis Pesticidal Crystal Proteins. Microbiology and Molecular Biology Reviews. vol. 62, No. 3, pp. 807-813.

Estruch, J. et al 1996. Vip3A, a novel Bacillus thuringiensis vegetative insecticidal protein with a wide spectrum of activities against lepidopteran insects. PNAS 93:5389-5394.

Hernandez-Martinez, P.; et al., 2013, "Insecticidal activity of Vip3Aa, Vip3Ad, Vip3Ae, and Vip3Af from Bacillus thuringiensis against lepidopteran corn pests," J. Inv. Pathol. Feb. 20, 2013.

Lee, M.; et al. 2003, "The mode of action of the Bacillus thuringiensis vegetative insecticidal protein Vip3A differs from that of Cry1Ab δ-endotoxin," Appl. Env. Microbiol. 69:4648-4657.

Li, C,; et al. 2007, "Bacillus thuringiensis Vip3 mutant proteins: insecticidal activity and trypsin sensitivity," Biocontrol Sci. Technol. 17:699-708.

Palma, L.; et al 2012, "Vip3C, A novel class of vegetative insecticidal proteins from Bacillus thuringiensis," Appl. Env. Microbiol. 78:7163-7165.

Rang, C, Gil, P, Neisner, N, Van Rie, J, Frutos, R. (2005), "Novel Vip3-related Protein From Bacillus Thuringiensis," Applied Environmental Microbiology. vol. 71, Issue 10, pp. 6276-6281.

Singh, G. et al. 2010, "Mode of action of vegetative insecticidal protein of Bacillus thuringiensis: interaction with ribosomal S2 protein triggers larvicidal activity in Spodoptera," Appl. Env. Microbial. Sep 10, 2010.

(Continued)

*Primary Examiner* — Medina A Ibrahim

(57) ABSTRACT

DIG-657 vegetative insecticidal toxins, polynucleotides encoding such toxins, use of such toxins to control pests, and transgenic plants that produce such toxins are disclosed. The invention includes DIG-657 variants, fragments and analogs.

4 Claims, 1 Drawing Sheet

Specification includes a Sequence Listing.

(56) References Cited

OTHER PUBLICATIONS

Yu, C.G., et al., "The Bacillus thuringiensis vegetative insecticidal protein Vip3A lyses midgut epithelium cells of susceptible insects," Appl Environ Microbiol, 1997. 63(2): pp 532-6.
Written Opinion for International Application PCT/US15/035914, dated Dec. 1, 2015.
Genbank Accession AAV70653_Vip3Ba1 [Bacillus thuringeiensis].
Genbank Accession DD319826_Novel Vip3 Toxins and Methods of Use.
Genbank Accession AR559867_Sequence 83 from U.S. Pat. No. 6,752,992.
Genbank Accession AR339977_Sequence 83 from U.S. Pat. No. 6,570,005.
Genbank Accession BD128377_Toxin active on Ostrinianubilalis.
Genbank Accession BD062624_Toxins active against pests.
Genbank Accession AR205869_Sequence 83 from U.S. Pat. No. 6,369,213.
Genbank Accession AR559877_Sequence 103 from U.S. Pat. No. 6,752,992.
Genbank Accession AR339987_Sequence 103 from U.S. Pat. No. 6,570,005.
Genbank Accession AY823271_Bacillus thuringiensis strain ucr8 Vip3Ba1 (vip3Ba1) gene.
Genbank Accession EF439819_Bacillus thuringiensis Vip3Bb2 (vip3Bb2) gene.
Genbank Accession HM016910_Bacillus thuringiensis strain M199 vegetative insecticidal protein gene.
Genbank Accession DQ241674_Bacillus thuringiensis isolate BtAL insecticidal protein Vip3A (vip3A) gene.

* cited by examiner

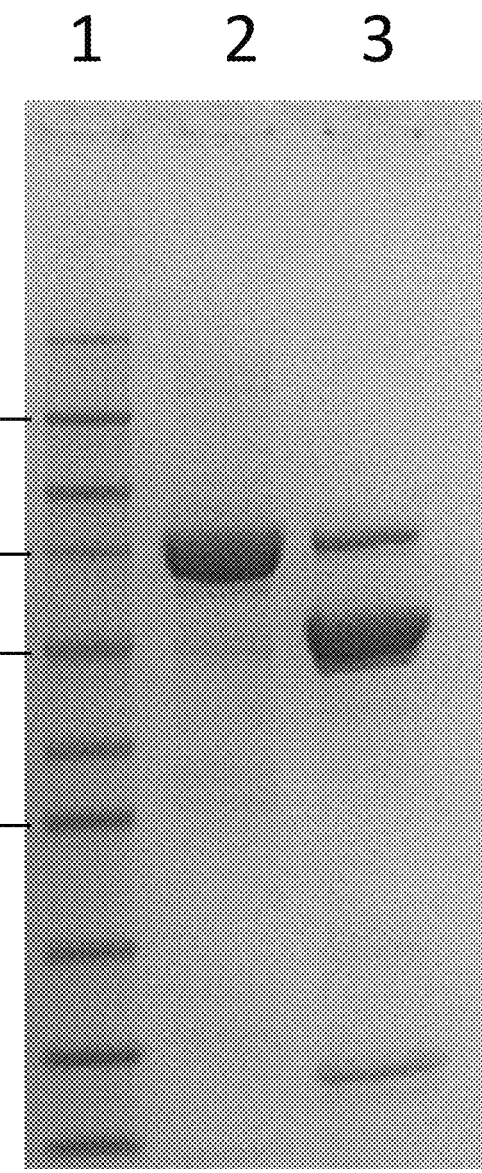

```
                          SEQUENCE LISTING

<160> NUMBER OF SEQ ID NOS: 13

<210> SEQ ID NO 1
<211> LENGTH: 2412
<212> TYPE: DNA
<213> ORGANISM: Bacillus thuringiensis

<400> SEQUENCE: 1
atggtacaaa aatggatgca aaggatgata attgtggata ataataaatt aaatgtaaga      60
gctttaccaa gctttattga ttatttaac ggtatttatg gatttgccac tggtatcaaa     120
gatattatgg gaatgatttt taaaacagat acaggtggta gtaatttaac attagatgag    180
attttaaaga atcaaaattt actaaatgat atctcaggta agctcgatgg aattaatgga    240
gatttagggg atcttattgc acaagggaac ttgaattcag aattagctaa ggaattgcta    300
aaaatctcta atgagcagaa tcaaatgtta aatcatgtta atgctcaact taatgcaatc    360
aattcaacac ttaatatata tcttccaaaa attacatcta tgttaaatga ggtgatgaag    420
caaaaccatg ttttaagtct acaaatagaa tttcttagta agcaattgca ggaaatttca    480
gataaacttg atattatcaa cttaaacgta ttgattaact ctacattaac agagattact    540
cctgcttatc aacgtattaa atatgtaaac gaaaaatttg atgaattgac ttctactgta    600
gagaaaaatc caaaatcata tcaagataac gttactaaag aagttattga aaacttaaat    660
gagctaactg agttggcgaa aagtgttacc aaaaatgata tggatagttt tgaattttat    720
cttcaaactt tccatgatgt aatgactgga ataaatttat tcggccgctc agcattaaaa    780
actgcttcag aattaattac aaaagaaaat gtcacgacaa ggggaagtga gataggaaaa    840
gtttataatt tcttaattgt tttaacttct ttacaagcaa aagcttttct cactttaact    900
gcatgtcgaa agttattagg tttaacagat atcgattata ctcaaattat gaatcatcat    960
atagatggtc aaaaaagaga atttcgtatt aatattcttc caacactttc taataatttt   1020
tctaatccta gttattcaaa aaatagagga agtgatatcg atgatccaat tgttgtgtta   1080
gaagcagcac ctggatatgc cttaatagga tttgaaattc taaacgatcc acttccaatt   1140 ttaaaggat atcaggctag gttaaaacca aattatcaag ttgacaggga gtcgatgtca    1200
gaaacgattt atggggacat tcataaatta ttttgcccaa aacagctgga gcaaaaatat   1260
tatattaaag atattgaatt tcctgagggc tatgtaatta ctaaaatcgt ttttgaaaaa   1320
aggctaaatc aattggggta tgaggtaaca gcaaattttt atgacccgtc tacaggaagt   1380
atcgatttaa ataaggttaa agtagaatct tggaaggaaa agtcttgcga ggaggattcc   1440
tgcgaagatg agtatagtat tataaaggcc gaaacggatg gcatttatat gccattaggc   1500
gtagtaagtg agactttttt aacccctatt tatggttttg gattaacagt tgacgaaaaa   1560
aatcaaaaaa taactttaac aggtaaatcc tatttacgtg aatccttact agaaacagac   1620
ttacttaaca atgaaacata tttaattgct tcaccagacg ttatattag tagtattgta    1680 gaaaactgga atataacatc agataatact gggtcttgga gagcaaataa taataatgca   1740
tttgtcgata aggcagatac tataaaagga tcaagttctc tgtatactca taaagatggg   1800
gaattctcgc aattattgg aaataagcta aaacctaaaa ctaattatgt tattcaatat    1860
gttataaaag gaagacctgc tatttattta aaaaataata aagatacttt atttgaggat   1920
```

```
accaaaaata actttagcga ttttcagact gtaactaaaa aattcaattc aggagtaaat    1980
ccttcggaaa tttatttcct tttaaaaat caaagtgaat acgaagcctg gggaaataac    2040
tttattattt tagaaattaa atcgcttgaa ttcttgccac aaatgctgaa gcctgaggat    2100
tggataccat caggaaatgt gcaaatgaaa gatggaggac gcctagagat tttgggagat    2160
ggttatttta acaattcat taaattggaa aatgattcaa cctatcatct aagattatct     2220
gttaagggaa caggtagggt atctataatt gatgaatcta aatatttact ttttgtaaat    2280
gttaaggatg aagatcttac tagagttatt aaaaatacct cttcaaaggg tgagtgtttt    2340
atagctcttg agggtactta tgtagaaaat tcaagtacta ttttctctaa tgtatctatt    2400
gttaaagagt ag                                                        2412
```

<210> SEQ ID NO 2
<211> LENGTH: 803
<212> TYPE: PRT
<213> ORGANISM: Bacillus thuringiensis

<400> SEQUENCE: 2

```
Met Val Gln Lys Trp Met Gln Arg Met Ile Ile Val Asp Asn Asn Lys
1               5                   10                  15

Leu Asn Val Arg Ala Leu Pro Ser Phe Ile Asp Tyr Phe Asn Gly Ile
            20                  25                  30

Tyr Gly Phe Ala Thr Gly Ile Lys Asp Ile Met Gly Met Ile Phe Lys
        35                  40                  45

Thr Asp Thr Gly Gly Ser Asn Leu Thr Leu Asp Glu Ile Leu Lys Asn
    50                  55                  60

Gln Asn Leu Leu Asn Asp Ile Ser Gly Lys Leu Asp Gly Ile Asn Gly
65                  70                  75                  80

Asp Leu Gly Asp Leu Ile Ala Gln Gly Asn Leu Asn Ser Glu Leu Ala
                85                  90                  95

Lys Glu Leu Leu Lys Ile Ser Asn Glu Gln Asn Gln Met Leu Asn His
            100                 105                 110

Val Asn Ala Gln Leu Asn Ala Ile Asn Ser Thr Leu Asn Ile Tyr Leu
        115                 120                 125

Pro Lys Ile Thr Ser Met Leu Asn Glu Val Met Lys Gln Asn His Val
    130                 135                 140

Leu Ser Leu Gln Ile Glu Phe Leu Ser Lys Gln Leu Gln Glu Ile Ser
145                 150                 155                 160

Asp Lys Leu Asp Ile Ile Asn Leu Asn Val Leu Ile Asn Ser Thr Leu
                165                 170                 175

Thr Glu Ile Thr Pro Ala Tyr Gln Arg Ile Lys Tyr Val Asn Glu Lys
            180                 185                 190

Phe Asp Glu Leu Thr Ser Thr Val Glu Lys Asn Pro Lys Ser Tyr Gln
        195                 200                 205

Asp Asn Val Thr Lys Glu Val Ile Glu Asn Leu Asn Glu Leu Thr Glu
    210                 215                 220

Leu Ala Lys Ser Val Thr Lys Asn Asp Met Asp Ser Phe Glu Phe Tyr
225                 230                 235                 240

Leu Gln Thr Phe His Asp Val Met Thr Gly Asn Asn Leu Phe Gly Arg
                245                 250                 255

Ser Ala Leu Lys Thr Ala Ser Glu Leu Ile Thr Lys Glu Asn Val Thr
            260                 265                 270

Thr Arg Gly Ser Glu Ile Gly Lys Val Tyr Asn Phe Leu Ile Val Leu
        275                 280                 285
```

-continued

```
Thr Ser Leu Gln Ala Lys Ala Phe Leu Thr Leu Thr Ala Cys Arg Lys
    290                 295                 300

Leu Leu Gly Leu Thr Asp Ile Asp Tyr Thr Gln Ile Met Asn His His
305                 310                 315                 320

Ile Asp Gly Gln Lys Arg Glu Phe Arg Ile Asn Ile Leu Pro Thr Leu
                325                 330                 335

Ser Asn Asn Phe Ser Asn Pro Ser Tyr Ser Lys Asn Arg Gly Ser Asp
                340                 345                 350

Ile Asp Asp Pro Ile Val Val Leu Glu Ala Ala Pro Gly Tyr Ala Leu
            355                 360                 365

Ile Gly Phe Glu Ile Leu Asn Asp Pro Leu Pro Ile Leu Lys Gly Tyr
    370                 375                 380

Gln Ala Arg Leu Lys Pro Asn Tyr Gln Val Asp Arg Glu Ser Met Ser
385                 390                 395                 400

Glu Thr Ile Tyr Gly Asp Ile His Lys Leu Phe Cys Pro Lys Gln Leu
                405                 410                 415

Glu Gln Lys Tyr Tyr Ile Lys Asp Ile Glu Phe Pro Glu Gly Tyr Val
                420                 425                 430

Ile Thr Lys Ile Val Phe Glu Lys Arg Leu Asn Gln Leu Gly Tyr Glu
            435                 440                 445

Val Thr Ala Asn Phe Tyr Asp Pro Ser Thr Gly Ser Ile Asp Leu Asn
    450                 455                 460

Lys Val Lys Val Glu Ser Trp Lys Glu Lys Ser Cys Glu Glu Asp Ser
465                 470                 475                 480

Cys Glu Asp Glu Tyr Ser Ile Ile Lys Ala Glu Thr Asp Gly Ile Tyr
                485                 490                 495

Met Pro Leu Gly Val Val Ser Glu Thr Phe Leu Thr Pro Ile Tyr Gly
            500                 505                 510

Phe Gly Leu Thr Val Asp Glu Lys Asn Gln Lys Ile Thr Leu Thr Gly
    515                 520                 525

Lys Ser Tyr Leu Arg Glu Ser Leu Leu Glu Thr Asp Leu Leu Asn Asn
530                 535                 540

Glu Thr Tyr Leu Ile Ala Ser Pro Asp Gly Tyr Ile Ser Ser Ile Val
545                 550                 555                 560

Glu Asn Trp Asn Ile Thr Ser Asp Asn Thr Gly Ser Trp Arg Ala Asn
                565                 570                 575

Asn Asn Asn Ala Phe Val Asp Lys Ala Asp Thr Ile Lys Gly Ser Ser
            580                 585                 590

Ser Leu Tyr Thr His Lys Asp Gly Glu Phe Ser Gln Phe Ile Gly Asn
    595                 600                 605

Lys Leu Lys Pro Lys Thr Asn Tyr Val Ile Gln Tyr Val Ile Lys Gly
610                 615                 620

Arg Pro Ala Ile Tyr Leu Lys Asn Asn Lys Asp Thr Leu Phe Glu Asp
625                 630                 635                 640

Thr Lys Asn Asn Phe Ser Asp Phe Gln Thr Val Thr Lys Lys Phe Asn
                645                 650                 655

Ser Gly Val Asn Pro Ser Glu Ile Tyr Phe Leu Phe Lys Asn Gln Ser
            660                 665                 670

Glu Tyr Glu Ala Trp Gly Asn Asn Phe Ile Ile Leu Glu Ile Lys Ser
    675                 680                 685

Leu Glu Phe Leu Pro Gln Met Leu Lys Pro Glu Asp Trp Ile Pro Ser
690                 695                 700
```

-continued

```
Gly Asn Val Gln Met Lys Asp Gly Gly Arg Leu Glu Ile Leu Gly Asp
705                 710                 715                 720

Gly Tyr Phe Lys Gln Phe Ile Lys Leu Glu Asn Asp Ser Thr Tyr His
            725                 730                 735

Leu Arg Leu Ser Val Lys Gly Thr Gly Arg Val Ser Ile Ile Asp Glu
        740                 745                 750

Ser Lys Tyr Leu Leu Phe Val Asn Val Lys Asp Glu Asp Leu Thr Arg
    755                 760                 765

Val Ile Lys Asn Thr Ser Ser Lys Gly Glu Cys Phe Ile Ala Leu Glu
770                 775                 780

Gly Thr Tyr Val Glu Asn Ser Ser Thr Ile Phe Ser Asn Val Ser Ile
785                 790                 795                 800

Val Lys Glu

<210> SEQ ID NO 3
<211> LENGTH: 2412
<212> TYPE: DNA
<213> ORGANISM: Artificial Sequence
<220> FEATURE:
<223> OTHER INFORMATION: synthesized full length coding region

<400> SEQUENCE: 3
atggtgcaga aatggatgca gcggatgata attgtagata caacaagct caacgttcgt       60 gcattgccgt ctttcataga ctatttcaac ggcatatatg gttcgccac cggcatcaag      120 gacatcatgg gaatgatctt caagaccgac acgggtggat ctaatctgac cctcgatgag      180
atcttgaaaa atcagaatct gctgaatgac atctcaggga actagacgg tattaacggc      240 gaccttggcg acttgattgc ccaggggaac ctaaactctg aactcgccaa ggaacttctc      300
aagattagca cgaacaaaa tcagatgctc aaccatgtga atgcacaatt gaatgcgatc      360
aatagtactc tcaacatcta ccttcccaag atcacatcca tgctgaacga ggttatgaag      420
caaaaccatg tgttatcgct gcagattgag ttcctgtcaa agcagttgca agagatttcc      480
gataagcttg acatcatcaa cttaaacgtc ctcatcaatt cgaccctcac cgaaattacc      540
cctgcgtatc agagaattaa gtacgtcaac gaaaagtttg acgagctgac cagtaccgtg      600
gagaaaaacc ccaagtcata tcaggataat gtcactaagg aagttattga aaacctcaat      660
gagcttacgg agctggcgaa aagcgtgacg aaaaacgata tggatagctt cgagttttac      720
ctccaaacct ccatgacgt aatgaccggg aacaacctct cgggaggtc agcgctcaag      780 acagcctccg agttaatcac gaaggagaac gtcacaaccc ggggttcaga aattgggaag      840
gtatacaact tcctaatcgt gcttacgagc cttcaagcta aagctttcct cacactgacg      900
gcctgccgga aactacttgg gctgaccgac atcgactata tcagattat gaatcaccac      960 atcgacggtc aaaagagaga gtttcgcatt aacattctcc caacgctcag taacaacttc     1020
tccaatccgt cgtattccaa aaaccgaggc tcagatattg acgatcctat tgtcgtcttg     1080
gaggcagcgc cagggtacgc actcatcggc ttcgaaatct taaacgaccc gctgcccatc     1140
cttaagggtt atcaggccag gctgaagccg aactaccagg tggaccgcga atccatgtcc     1200
gaaacgatct acggcgacat ccacaagctg ttctgtccga gcagctcga acaaaagtac     1260 tacattaaag acatcgagtt cccagaggga tatgtgatta cgaaaattgt gttcgaaaag     1320
aggctcaacc aacttggata tgaggtcaca gctaatttct acgatccttc gactggctct     1380
atcgatttga ataaggtgaa ggttgaatcg tggaaggaga aaagctgtga ggaagatagt     1440
tgcgaggatg aatattcaat cataaaggcg gaaacagatg gaatatacat gccgctcggc     1500
```

```
gttgtcagcg agactttcct gaccccctatc tacggttttg gtctaacagt cgacgagaaa    1560
aaccagaaga tcactctgac cggtaaaagt taccttcgcg agtcgctgct ggagactgac    1620
ctgctgaaca acgagactta cttgatcgct agcccagacg ggtacattag ctctatcgtc    1680
gaaaactgga atatcacctc tgataatact ggctcgtgga gggccaataa caacaatgcg    1740
tttgtggata agcagatac aatcaaaggc tcaagcagcc tctacacgca aaggatgga    1800 gagttttccc agtttatagg caacaagttg aagccaaaga cgaattacgt tatacagtac    1860
gtgatcaagg gcaggccagc catatacttg aaaaacaata aggacacgct tttcgaagat    1920
acgaagaata acttctccga tttccaaacc gttacaaaga agttcaatag tggagtgaat    1980
cctagcgaga tctactttct gttcaaaaac caatctgagt acgaggcttg gggcaacaac    2040
ttcataattc tagagataaa gtccctggag tttctgcccc agatgctgaa gcccgaggat    2100
tggatcccct ccggcaatgt acagatgaag gacggcggac gcctagagat tctcggcgac    2160
ggctacttta gcagttcat caagttagag aacgactcga cttatcacct tcgtctctca    2220
gtgaagggta cagggagagt cagcatcatc gacgagtcga agtaccttttt gttcgtcaac    2280 gttaaggacg aggacctgac acgagtcata aagaatacca gcagtaaggg cgagtgcttt    2340
atcgctttgg agggcactta tgttgagaac tcctctacca tattctccaa tgtttctata    2400
gtgaaggagt ga                                                         2412

<210> SEQ ID NO 4
<211> LENGTH: 2412
<212> TYPE: DNA
<213> ORGANISM: Artificial Sequence
<220> FEATURE:
<223> OTHER INFORMATION: synthesized full length coding region

<400> SEQUENCE: 4
atggcccaga agtggatgca acgcatgatc atcgtggata caacaagct gaacgtccgt      60 gccctgccga gcttcatcga ctacttcaac ggcatctacg gcttcgcgac cggcattaaa     120
gacattatgg gcatgatctt caagaccgac acgggcggta gcaacttgac cctggacgaa     180
attctgaaga atcagaatct gctcaacgat atcagcggca agctcgacgg cattaacggg     240
gatctgggcg acctgatcgc ccaagggaac ctgaacagcg agctggcgaa agagctgttg     300
aagatctcca cgaacagaa ccagatgctg aaccacgtga atgcccaact gaacgccatc     360
aactcgaccc tgaacatcta cttgcccaag atcacctcga tgttgaacga ggtgatgaag     420
cagaaccatg tgctgagcct gcagattgag ttcctgagca gcagctgca ggaaatctcc     480 gacaagctgg atatcatcaa cctgaatgtg ctgatcaata gcaccttgac cgagatcacc     540
ccggcctatc agcgcatcaa gtacgtgaac gagaagttcg acgaactgac cagcaccgtc     600
gaaaagaatc ccaagtcgta ccaggacaat gtcaccaaag aagtgatcga acttgaac     660 gagctcaccg aactggccaa atcggtacg aagaacgaca tggactcgtt cgaattctat     720
ctgcagacct tccacgacgt gatgaccggc aacaacctgt tcggccgcag cgccctgaaa     780
accgcctcgg aactgatcac gaaagagaat gtgaccaccc gtggctccga gatcggcaag     840
gtgtacaact tcctgattgt cctgacctcg ctgcaggcga aggcgtttct gaccttgacg     900
gcctgccgta agctgttggg cctgaccgac attgactaca cgcagatcat gaatcaccac     960
atcgacggtc agaagcggga attccgcatc aacatcctgc cgaccctgag caataacttc    1020 tccaaccccca gctacagcaa gaaccggggc agcgatatcg acgacccgat cgtggtcctc    1080
```

| | |
|---|---|
| gaagcggcgc cggctacgc cctgatcggc ttcgagatcc tgaacgaccc gttgccgatc | 1140 |
| ctgaaagggt accaagcgcg cctgaagccg aattaccagg tggatcgcga gtcgatgagc | 1200 |
| gaaaccattt acggcgacat tcacaagctg ttctgcccca agcaactcga acagaagtac | 1260 |
| tatatcaagg acatcgaatt cccggaaggc tacgtgatta ccaagatcgt ctttgaaaag | 1320 |
| cgcctgaacc agctgggtta tgaggtcacc gccaacttct acgacccgag cacgggtagc | 1380 |
| atcgacctga taaggtgaa ggtggaaagc tggaaagaga gtcgtgcga agaggattcg | 1440 |
| tgcgaggacg agtatagcat catcaaggcg gaaaccgatg gcatctacat gccgctcggc | 1500 |
| gtcgtcagcg aaacctttct caccccgatc tacgggtttg gcttgaccgt ggatgaaaag | 1560 |
| aaccagaaaa tcaccctgac cggtaagagc tatctccgcg agtccttgct ggaaacggac | 1620 |
| ctgttgaaca cgaaaccta cctgattgcc agcccggatg ttatatctc gtcgattgtg | 1680 |
| gagaactgga acatcaccag cgacaacacc ggctcgtggc gtgccaacaa taacaatgcc | 1740 |
| ttcgtcgaca aggccgatac gatcaagggt agctccagcc tgtacaccca caaagacggt | 1800 |
| gaatttagcc agtttattgg caataagttg aagcccaaga ccaattacgt catccaatac | 1860 |
| gtcattaagg gccgtccggc gatctatctg aaaaacaaca aggacaccct cttcgaggat | 1920 |
| accaagaaca acttcagcga cttccagacc gtgaccaaga aattcaattc cggtgtgaac | 1980 |
| ccgtccgaaa tctatttcct gttcaaaaac cagtcggaat acgaggcctg gggcaacaac | 2040 |
| tttatcatcc tggagatcaa gagcctggag tttctgccgc aaatgctgaa acccgaggat | 2100 |
| tggattccca gcgggaacgt gcagatgaag gatggtggcc gcctcgaaat cttgggcgac | 2160 |
| ggctacttca gcagttcat caagttggaa acgacagca cctaccatct gcggctgtcc | 2220 |
| gtcaagggca ccggccgtgt gtccatcatc gacgagtcca gtatctgct cttcgtgaac | 2280 |
| gtgaaggatg aggatctgac ccgcgtgatc aagaacacca gcagcaaagg ggaatgtttc | 2340 |
| atcgccctgg aaggcacgta cgtcgagaac tccagcacca tcttcagcaa cgtgtccatc | 2400 |
| gtgaaagagt ga | 2412 |

<210> SEQ ID NO 5
<211> LENGTH: 2412
<212> TYPE: DNA
<213> ORGANISM: Artificial Sequence
<220> FEATURE:
<223> OTHER INFORMATION: synthesized full length coding region

<400> SEQUENCE: 5

| | |
|---|---|
| atggtgcaga agtggatgca gaggatgata atcgttgaca ataataaatt aaacgtgagg | 60 |
| gcactgccga gcttcatcga ctacttcaac ggcatctacg gcttcgccac cggcatcaag | 120 |
| gacatcatgg gcatgatctt caagaccgac accggaggca gcaacctgac cctggacgag | 180 |
| atcctcaaga atcaaaacct cctgaacgac atcagcggga agctggacgg aattaatggc | 240 |
| gatcttggag acctgatcgc ccaaggcaac ctcaactccg agctggccaa ggagctgctg | 300 |
| aagatttcca acgagcagaa tcaaatgctg aaccacgtga acgctcagct gaacgcaatc | 360 |
| aactcaaccc tgaacatcta cctgcccaag atcacgtcca tgctgaacga ggtgatgaag | 420 |
| cagaaccatg tgctgtccct ccagatagag ttcctgagca agcagctgca agagatatcc | 480 |
| gacaagctgg acatcatcaa cctcaacgtg ctgatcaaca gcaccctcac cgagatcacc | 540 |
| cctgcgtacc agaggattaa atacgtgaac gagaagttcg acgaactgac ctccaccgtg | 600 |
| gagaagaacc ccaaatccta ccaagacaac gtcaccaagg aggtgatcga gaacctgaac | 660 |
| gagctgacgg agctggcgaa gagcgtcacc aagaacgaca tggactcctt cgagttctac | 720 |

```
ctccagacct tccacgacgt gatgaccggg aataatctgt tcgggcgctc agcattaaag      780
accgcgagcg aattaatcac caaggagaac gtgaccacca gaggctccga gatcggcaag      840
gtgtacaact tcctgatcgt gctcacctcc ctgcaagcga aggcgttcct caccctgacc      900
gcgtgtagga agctgctggg cctgaccgac atcgattaca cccagatcat gaaccaccac      960
atcgacggcc agaagaggga gtttaggatt aatatcctgc cgaccctgtc caataatttc     1020
tccaacccga gctactccaa aaatagaggc tcggacatcg acgacccat cgtggtgctg       1080 gaggcagccc ctggctacgc cctgatcggc ttcgagatcc tgaacgaccc gctgccgatc     1140
ctcaagggct accaagcgag gctgaaacca aactaccaag tggataggga gagcatgtca     1200
gagaccatct acggggacat ccataaactg ttctgcccaa gcagctgga gcaaaaatat      1260 tacattaaag atatcgagtt cccggagggc tacgtgatca ccaagatcgt gttcgagaag     1320
aggctgaatc aactgggcta cgaagtgacc gccaacttct acgacccgag caccggctcc     1380
atcgacctga caaggtgaa ggtggagagc tggaaggaga agtcctgtga ggaggactcc      1440
tgcgaggacg agtactccat catcaaggcc gagaccgacg ggatctacat gccgctgggc     1500
gtggtgagcg agaccttcct gaccccgatc tacgggtttg gcctcaccgt ggacgagaaa     1560
aatcaaaaaa taaccctgac cggcaagtcc tacctgaggg agtccctgct ggagaccgac     1620
ctgctgaaca atgaaaccta cctcatcgcc agcccagacg gctacatcag cagcatcgtc     1680
gagaactgga atataacctc cgacaacacc gggagctgga gggccaataa taataatgcc     1740
ttcgtggaca aggcggatac tataaaaggc tcaagcagcc tgtacaccca taaagacggc     1800
gagttctcgc agttcatcgg caacaagctg aagcccaaga ccaactacgt catccagtac     1860
gttataaaag gaaggcctgc gatctacctg aaaaataata aagacaccct gttcgaggac     1920
accaaaaata acttcagcga cttccagacc gtgaccaaga gttcaactc tggcgtgaac      1980 ccgagcgaaa tctacttcct gttcaagaat caatccgagt acgaggcctg ggcaacaac      2040 ttcatcatcc tggaaattaa atccctggag ttcctgccgc agatgctgaa gccggaggac     2100
tggataccga gcggcaacgt gcagatgaaa gacggtggaa ggctggagat cctgggcgac     2160
ggctacttca gcagttcat taaactggag aacgacagca cctaccacct gaggctgagc     2220
gtgaagggaa ctgggagggt gtcgatcatc gacgagtcca agtacctgct gttcgtgaac     2280
gtgaaggacg aggacctgac gagggtgatt aaaaatacct cctccaaggg cgagtgcttc     2340
atcgcgctgg aaggcaccta cgtggagaac agctcaacca tcttctccaa cgtgagcatc     2400
gtgaaggagt ga                                                         2412

<210> SEQ ID NO 6
<211> LENGTH: 1800
<212> TYPE: DNA
<213> ORGANISM: Artificial Sequence
<220> FEATURE:
<223> OTHER INFORMATION: synthesized full length coding region

<400> SEQUENCE: 6
atgtcctacc aagacaacgt caccaaggag gtgatcgaga acctgaacga gctgacggag       60
ctggcgaaga gcgtcaccaa gaacgacatg gactccttcg agttctacct ccagaccttc      120
cacgacgtga tgaccgggaa taatctgttc gggcgctcag cattaaagac cgcgagcgaa      180
ttaatcacca aggagaacgt gaccaccaga ggctccgaga tcggcaaggt gtacaacttc      240
ctgatcgtgc tcacctccct gcaagcgaag gcgttcctca ccctgaccgc gtgtaggaag      300
```

```
ctgctgggcc tgaccgacat cgattacacc cagatcatga accaccacat cgacggccag    360
aagagggagt ttaggattaa tatcctgccg accctgtcca ataatttctc caacccgagc    420
tactccaaaa atagaggctc ggacatcgac gaccccatcg tggtgctgga ggcagcccct    480
ggctacgccc tgatcggctt cgagatcctg aacgacccgc tgccgatcct caagggctac    540
caagcgaggc tgaaaccaaa ctaccaagtg datagggaga gcatgtcaga gaccatctac    600
ggggacatcc ataaactgtt ctgcccaaag cagctggagc aaaaatatta cattaaagat    660
atcgagttcc ggagggcta cgtgatcacc aagatcgtgt tcgagaagag gctgaatcaa    720
ctgggctacg aagtgaccgc caacttctac gacccgagca ccggctccat cgacctgaac    780
aaggtgaagg tggagagctg aaggagaag tcctgtgagg aggactcctg cgaggacgag    840
tactccatca tcaaggccga gaccgacggg atctacatgc cgctgggcgt ggtgagcgag    900
accttcctga ccccgatcta cgggtttggc ctcaccgtgg acgagaaaaa tcaaaaaata    960
accctgaccg gcaagtccta cctgagggag tccctgctgg agaccgacct gctgaacaat    1020
gaaacctacc tcatcgccag cccagacggc tacatcagca gcatcgtcga aactggaat    1080 ataacctccg acaacaccgg gagctggagg gccaataata taatgccctt cgtggacaag    1140
gcggatacta taaaaggctc aagcagcctg tacacccata agacggcga gttctcgcag    1200 ttcatcggca acaagctgaa gcccaagacc aactacgtca tccagtacgt tataaaagga    1260
aggcctgcga tctacctgaa aaataataaa gacaccctgt cgaggacac aaaaataac    1320 ttcagcgact ccagaccgt gaccaagaag ttcaactctg gcgtgaaccc gagcgaaatc    1380
tacttcctgt tcaagaatca atccgagtac gaggcctggg gcaacaactt catcatcctg    1440
gaaattaaat ccctggagtt cctgccgcag atgctgaagc cggaggactg gataccgagc    1500
ggcaacgtgc agatgaaaga cggtggaagg ctggagatcc tgggcgacgg ctacttcaag    1560
cagttcatta aactggagaa cgacagcacc taccacctga ggctgagcgt gaagggaact    1620
gggagggtgt cgatcatcga cgagtccaag tacctgctgt cgtgaacgt gaaggacgag    1680 gacctgacga gggtgattaa aaataccctcc tccaagggcg agtgcttcat cgcgctggaa    1740
ggcacctacg tggagaacag ctcaaccatc ttctccaacg tgagcatcgt gaaggagtga    1800
```

<210> SEQ ID NO 7
<211> LENGTH: 599
<212> TYPE: PRT
<213> ORGANISM: Artificial Sequence
<220> FEATURE:
<223> OTHER INFORMATION: translated from synthesized full length coding region

<400> SEQUENCE: 7

```
Met Ser Tyr Gln Asp Asn Val Thr Lys Glu Val Ile Glu Asn Leu Asn
1               5                   10                  15

Glu Leu Thr Glu Leu Ala Lys Ser Val Thr Lys Asn Asp Met Asp Ser
            20                  25                  30

Phe Glu Phe Tyr Leu Gln Thr Phe His Asp Val Met Thr Gly Asn Asn
        35                  40                  45

Leu Phe Gly Arg Ser Ala Leu Lys Thr Ala Ser Glu Leu Ile Thr Lys
    50                  55                  60

Glu Asn Val Thr Thr Arg Gly Ser Glu Ile Gly Lys Val Tyr Asn Phe
65                  70                  75                  80

Leu Ile Val Leu Thr Ser Leu Gln Ala Lys Ala Phe Leu Thr Leu Thr
                85                  90                  95
```

-continued

```
Ala Cys Arg Lys Leu Leu Gly Leu Thr Asp Ile Asp Tyr Thr Gln Ile
                100                 105                 110

Met Asn His His Ile Asp Gly Gln Lys Arg Glu Phe Arg Ile Asn Ile
            115                 120                 125

Leu Pro Thr Leu Ser Asn Asn Phe Ser Asn Pro Ser Tyr Ser Lys Asn
        130                 135                 140

Arg Gly Ser Asp Ile Asp Asp Pro Ile Val Val Leu Glu Ala Ala Pro
145                 150                 155                 160

Gly Tyr Ala Leu Ile Gly Phe Glu Ile Leu Asn Asp Pro Leu Pro Ile
                165                 170                 175

Leu Lys Gly Tyr Gln Ala Arg Leu Lys Pro Asn Tyr Gln Val Asp Arg
            180                 185                 190

Glu Ser Met Ser Glu Thr Ile Tyr Gly Asp Ile His Lys Leu Phe Cys
        195                 200                 205

Pro Lys Gln Leu Glu Gln Lys Tyr Tyr Ile Lys Asp Ile Glu Phe Pro
    210                 215                 220

Glu Gly Tyr Val Ile Thr Lys Ile Val Phe Glu Lys Arg Leu Asn Gln
225                 230                 235                 240

Leu Gly Tyr Glu Val Thr Ala Asn Phe Tyr Asp Pro Ser Thr Gly Ser
                245                 250                 255

Ile Asp Leu Asn Lys Val Lys Val Glu Ser Trp Lys Glu Lys Ser Cys
            260                 265                 270

Glu Glu Asp Ser Cys Glu Asp Glu Tyr Ser Ile Ile Lys Ala Glu Thr
        275                 280                 285

Asp Gly Ile Tyr Met Pro Leu Gly Val Val Ser Glu Thr Phe Leu Thr
    290                 295                 300

Pro Ile Tyr Gly Phe Gly Leu Thr Val Asp Glu Lys Asn Gln Lys Ile
305                 310                 315                 320

Thr Leu Thr Gly Lys Ser Tyr Leu Arg Glu Ser Leu Leu Glu Thr Asp
                325                 330                 335

Leu Leu Asn Asn Glu Thr Tyr Leu Ile Ala Ser Pro Asp Gly Tyr Ile
            340                 345                 350

Ser Ser Ile Val Glu Asn Trp Asn Ile Thr Ser Asp Asn Thr Gly Ser
        355                 360                 365

Trp Arg Ala Asn Asn Asn Asn Ala Phe Val Asp Lys Ala Asp Thr Ile
    370                 375                 380

Lys Gly Ser Ser Ser Leu Tyr Thr His Lys Asp Gly Glu Phe Ser Gln
385                 390                 395                 400

Phe Ile Gly Asn Lys Leu Lys Pro Lys Thr Asn Tyr Val Ile Gln Tyr
                405                 410                 415

Val Ile Lys Gly Arg Pro Ala Ile Tyr Leu Lys Asn Asn Lys Asp Thr
            420                 425                 430

Leu Phe Glu Asp Thr Lys Asn Asn Phe Ser Asp Phe Gln Thr Val Thr
        435                 440                 445

Lys Lys Phe Asn Ser Gly Val Asn Pro Ser Glu Ile Tyr Phe Leu Phe
    450                 455                 460

Lys Asn Gln Ser Glu Tyr Glu Ala Trp Gly Asn Asn Phe Ile Ile Leu
465                 470                 475                 480

Glu Ile Lys Ser Leu Glu Phe Leu Pro Gln Met Leu Lys Pro Glu Asp
                485                 490                 495

Trp Ile Pro Ser Gly Asn Val Gln Met Lys Asp Gly Gly Arg Leu Glu
            500                 505                 510

Ile Leu Gly Asp Gly Tyr Phe Lys Gln Phe Ile Lys Leu Glu Asn Asp
```

```
                515                 520                 525
Ser Thr Tyr His Leu Arg Leu Ser Val Lys Gly Thr Gly Arg Val Ser
            530                 535                 540

Ile Ile Asp Glu Ser Lys Tyr Leu Leu Phe Val Asn Val Lys Asp Glu
545                 550                 555                 560

Asp Leu Thr Arg Val Ile Lys Asn Thr Ser Lys Gly Glu Cys Phe
                565                 570                 575

Ile Ala Leu Glu Gly Thr Tyr Val Glu Asn Ser Ser Thr Ile Phe Ser
            580                 585                 590

Asn Val Ser Ile Val Lys Glu
        595

<210> SEQ ID NO 8
<211> LENGTH: 2412
<212> TYPE: DNA
<213> ORGANISM: Artificial Sequence
<220> FEATURE:
<223> OTHER INFORMATION: synthesized full length coding region

<400> SEQUENCE: 8
```

| | | | | | |
|---|---|---|---|---|---|
| atggttcaaa | agtggatgca | agaatgata | attgttgaca | ataataaatt | aaatgttaga | 60 |
| gcacttccat | ctttcattga | ttactttaac | ggaatctatg | gatttgctac | tgggattaag | 120 |
| gatatcatgg | gaatgatctt | taagactgat | actggtggtt | ctaatcttac | tcttgatgag | 180 |
| atattgaaga | tcaaaatttt | gcttaatgac | atttctggca | agctggatgg | aattaatgga | 240 |
| gaccttggtg | atcttattgc | tcaaggaaac | cttaactctg | aacttgctaa | ggaacttctt | 300 |
| aagatttcaa | atgagcaaaa | tcaaatgttg | aaccatgtta | acgctcaact | taacgcaatc | 360 |
| aactctacac | ttaacatcta | tcttccaaag | attacttcaa | tgcttaatga | ggttatgaag | 420 |
| caaaaccacg | ttctttctct | tcaaattgaa | tttctttcta | gcaacttca | agagatttct | 480 |
| gataagctgg | atatcattaa | ccttaacgtt | tcattaact | ctactttgac | tgagattact | 540 |
| cctgcttacc | aaaggattaa | atacgttaac | gaaaagttcg | atgaactgac | ttctactgtt | 600 |
| gagaagaacc | caaagtctta | ccaagataac | gttactaagg | aagttattga | aaaccttaat | 660 |
| gagcttactg | agcttgctaa | gtctgttaca | aagaacgaca | tggattcatt | cgagttctat | 720 |
| cttcaaactt | tccatgatgt | tatgactggg | aataatcttt | tcgggaggtc | tgcattaaag | 780 |
| actgcttctg | aattaatcac | taaggaaaac | gtaactacta | gaggttctga | gattggaaag | 840 |
| gtgtataact | ttcttattgt | tcttacttca | cttcaagcta | aggctttcct | tactcttact | 900 |
| gcttgtagaa | agctccttgg | tcttactgac | attgattaca | ctcagattat | gaaccatcat | 960 |
| attgatggtc | aaaagagaga | gtttaggatt | aatatccttc | caactctttc | taataatttc | 1020 |
| tcaaatccat | cttactctaa | aaatagaggt | tctgatattg | atgatcctat | tgtagttctt | 1080 |
| gaagctgctc | ctggatacgc | tcttattgga | tttgagatac | ttaacgatcc | acttcctatt | 1140 |
| cttaagggtt | atcaagctag | acttaaacca | aactatcaag | ttgatagaga | gtctatgtca | 1200 |
| gagactatct | acggagatat | tcataaactc | ttttgcccaa | agcaacttga | gcaaaaatat | 1260 |
| tacattaaag | atattgaatt | tcctgaggga | tacgtcatta | ctaagatagt | ttttgaaaag | 1320 |
| agacttaatc | aacttggtta | cgaggttact | gctaactttt | acgatccatc | taccggatct | 1380 |
| attgatctta | acaaggttaa | ggttgaatct | tggaaggaaa | agtcttgcga | ggaggattct | 1440 |
| tgcgaagatg | agtattcaat | cattaaggct | gaaacagatg | gcatctatat | gccacttgga | 1500 |
| gtggtttctg | aaacttttct | tactcctatc | tatggtttcg | gacttactgt | tgatgagaag | 1560 |

| | |
|---|---|
| aatcaaaaaa taactttgac tgggaagtct tatcttagag aatctcttct tgaaactgat | 1620 |
| cttcttaaca atgaaactta ccttattgct tctccagacg gttacatttc ttctattgtt | 1680 |
| gagaactgga atataacttc tgacaatact ggatcttgga gagctaataa taataatgct | 1740 |
| tttgtggata aggctgatac tataaaaggt tcttcatctc tttacactca taaagatggt | 1800 |
| gagttttctc aattcattgg aaacaaactt aagcctaaga ccaattacgt tattcaatat | 1860 |
| gttataaaag ggagacctgc tatctatctt aaaaataata aagatactct tttcgaggat | 1920 |
| accaaaaata acttttctga ttttcaaact gttactaaga aattcaattc tggagttaat | 1980 |
| ccttctgaaa tctacttcct tttcaagaat caatctgaat acgaggcatg gggaaacaac | 2040 |
| tttatcattt tggaaattaa atcacttgag ttccttccac aaatgcttaa gcctgaggat | 2100 |
| tggattcctt ctggaaacgt tcagatgaaa gacggaggca gacttgagat tcttggagat | 2160 |
| ggttacttta agcaattcat taaattggag aatgattcaa cttaccatct gagactttct | 2220 |
| gttaagggaa ctggcagagt ttctatcatt gatgaatcta gtatcttct tttgtaaat | 2280 |
| gttaaggatg aggatctgac tagagtcatt aaaaatactt cttctaaggg tgagtgtttc | 2340 |
| attgctcttg agggaactta cgttgaaaac tcttctacca ttttctctaa tgtttcaata | 2400 |
| gttaaggagt ga | 2412 |

<210> SEQ ID NO 9
<211> LENGTH: 1800
<212> TYPE: DNA
<213> ORGANISM: Artificial Sequence
<220> FEATURE:
<223> OTHER INFORMATION: synthesized full length coding region

<400> SEQUENCE: 9

| | |
|---|---|
| atgtcttacc aagataacgt tactaaggaa gttattgaaa accttaatga gcttactgag | 60 |
| cttgctaagt ctgttacaaa gaacgacatg gattcattcg agttctatct tcaaactttc | 120 |
| catgatgtta tgactgggaa taatcttttc gggaggtctg cattaaagac tgcttctgaa | 180 |
| ttaatcacta aggaaaacgt aactactaga ggttctgaga ttggaaaggt gtataacttt | 240 |
| cttattgttc ttacttcact tcaagctaag gctttcctta ctcttactgc ttgtagaaag | 300 |
| ctccttggtc ttactgacat tgattacact cagattatga accatcatat tgatggtcaa | 360 |
| aagagagagt ttaggattaa tatccttcca actctttcta ataatttctc aaatccatct | 420 |
| tactctaaaa atagaggttc tgatattgat gatcctattg tagttcttga agctgctcct | 480 |
| ggatacgctc ttattggatt tgagatactt aacgatccac ttcctattct taagggttat | 540 |
| caagctagac ttaaaccaaa ctatcaagtt gatagagagt ctatgtcaga gactatctac | 600 |
| ggagatattc ataaactctt tgcccaaag caacttgagc aaaaatatta cattaaagat | 660 |
| attgaatttc tgagggata cgtcattact aagatagttt ttgaaaagag acttaatcaa | 720 |
| cttggttacg aggttactgc taacttttac gatccatcta ccggatctat tgatcttaac | 780 |
| aaggttaagg ttgaatcttg gaaggaaaag tcttgcgagg aggattcttg cgaagatgag | 840 |
| tattcaatca ttaaggctga aacagatggc atctatatgc cacttggagt ggtttctgaa | 900 |
| acttttctta ctcctatcta tggtttcgga cttactgttg atgagaagaa tcaaaaaata | 960 |
| actttgactg ggaagtctta tcttagagaa tctcttcttg aaactgatct tcttaacaat | 1020 |
| gaaacttacc ttattgcttc tccagacggt tacatttctt ctattgttga gaactggaat | 1080 |
| ataacttctg acaatactgg atcttggaga gctaataata ataatgcttt tgtggataag | 1140 |
| gctgatacta aaaaggttc ttcatctctt tacactcata aagatggtga gttttctcaa | 1200 |

-continued

```
ttcattggaa acaaacttaa gcctaagacc aattacgtta ttcaatatgt tataaaaggg    1260
agacctgcta tctatcttaa aaataataaa gatactcttt tcgaggatac caaaaataac    1320
ttttctgatt ttcaaactgt tactaagaaa ttcaattctg gagttaatcc ttctgaaatc    1380
tacttccttt tcaagaatca atctgaatac gaggcatggg gaaacaactt tatcattttg    1440
gaaattaaat cacttgagtt ccttccacaa atgcttaagc ctgaggattg gattccttct    1500
ggaaacgttc agatgaaaga cggaggcaga cttgagattc ttgggatgg ttactttaag     1560 caattcatta aattggagaa tgattcaact taccatctga gactttctgt taagggaact    1620
ggcagagttt ctatcattga tgaatctaag tatcttcttt ttgtaaatgt taaggatgag    1680
gatctgacta gagtcattaa aaatacttct tctaagggtg agtgtttcat tgctcttgag    1740
ggaacttacg ttgaaaactc ttctaccatt ttctctaatg tttcaatagt taaggagtga    1800
```

<210> SEQ ID NO 10
<211> LENGTH: 2625
<212> TYPE: DNA
<213> ORGANISM: Artificial Sequence
<220> FEATURE:
<223> OTHER INFORMATION: synthesized full length coding region

<400> SEQUENCE: 10

```
atgttagcta gacaaggtgg atctcttaga gcttctcaat gtaacgctgg acttgctaga     60
agagttgagg ttggtgctct tgttgttcct agaccaattt ctgttaacga cgttgttcca    120
cacgtctatt ctgctcctct ttctgttgct agacgttctt gctctaagtc ctctattaga    180
agtactagaa ggcttcaaac tactgtttgc tcaatggttc aaaagtggat gcaaagaatg    240
ataattgttg acaataataa attaaatgtt agagcacttc catctttcat tgattacttt    300
aacggaatct atggatttgc tactgggatt aaggatatca tgggaatgat ctttaagact    360
gatactggtg ttctaatct tactcttgat gagatattga agaatcaaaa tttgcttaat     420
gacatttctg gcaagctgga tggaattaat ggagaccttg gtgatcttat tgctcaagga    480
aaccttaact ctgaacttgc taaggaactt cttaagattt caaatgagca aaatcaaatg    540
ttgaaccatg ttaacgctca acttaacgca atcaactcta cacttaacat ctatcttcca    600
aagattactt caatgcttaa tgaggttatg aagcaaaacc acgttctttc tcttcaaatt    660 gaatttctt ctaagcaact tcaagagatt tctgataagc tggatatcat taaccttaac     720
gttctcatta actctacttt gactgagatt actcctgctt accaaaggat taaatacgtt    780
aacgaaaagt tcgatgaact gacttctact gttgagaaga cccaaagtc ttaccaagat     840 aacgttacta aggaagttat tgaaaacctt aatgagctta ctgagcttgc taagtctgtt    900
acaaagaacg acatggattc attcgagttc tatcttcaaa ctttccatga tgttatgact    960
gggaataatc ttttcgggag gtctgcatta aagactgctt ctgaattaat cactaaggaa    1020
aacgtaacta ctagaggttc tgagattgga aaggtgtata actttcttat tgttcttact    1080
tcacttcaag ctaaggcttt cattactctt actgcttgta gaaagctcct tggtcttact    1140
gacattgatt acactcagat tatgaaccat catattgatg gtcaaaagag agagtttagg    1200
attaatatcc ttccaactct ttctaataat ttctcaaatc catcttactc taaaaataga    1260
ggttctgata ttgatgatcc tattgtagtt cttgaagctg ctcctggata cgctcttatt    1320
ggatttgaga tacttaacga tccacttcct attcttaagg ttatcaagc tagacttaaa     1380 ccaaactatc aagttgatag agagtctatg tcagagacta tctacggaga tattcataaa    1440
```

-continued

```
ctcttttgcc caaagcaact tgagcaaaaa tattacatta agatattga atttcctgag    1500 ggatacgtca ttactaagat agttttgaa aagagactta atcaacttgg ttacgaggtt    1560
actgctaact tttacgatcc atctaccgga tctattgatc ttaacaaggt taaggttgaa    1620
tcttggaagg aaaagtcttg cgaggaggat tcttgcgaag atgagtattc aatcattaag    1680
gctgaaacag atggcatcta tgccacttt ggagtggttt ctgaaacttt tcttactcct    1740
atctatggtt tcggacttac tgttgatgag aagaatcaaa aataactttt gactgggaag    1800
tcttatctta gagaatctct tcttgaaact gatcttctta acaatgaaac ttaccttatt    1860
gcttctccag acggttacat ttcttctatt gttgagaact ggaatataac ttctgacaat    1920
actggatctt ggagagctaa taataataat gcttttgtgg ataaggctga tactataaaa    1980
ggttcttcat ctcttacac tcataaagat ggtgagtttt ctcaattcat tggaaacaaa    2040
cttaagccta agaccaatta cgttattcaa tatgttataa aagggagacc tgctatctat    2100
cttaaaaata taaagatac tcttttcgag gataccaaaa ataacttttc tgattttcaa    2160
actgttacta agaaattcaa ttctggagtt aatccttctg aaatctactt ccttttcaag    2220
aatcaatctg aatacgaggc atggggaaac aactttatca ttttggaaat taaatcactt    2280
gagttccttc cacaaatgct taagcctgag gattggattc cttctggaaa cgttcagatg    2340
aaagacggag gcagacttga gattcttgga gatggttact ttaagcaatt cattaaattg    2400
gagaatgatt caacttacca tctgagactt tctgttaagg gaactggcag agtttctatc    2460
attgatgaat ctaagtatct tctttttgta aatgttaagg atgaggatct gactagagtc    2520
attaaaaata cttcttctaa gggtgagtgt tcattgctc ttgagggaac ttacgttgaa    2580
aactcttcta ccatttctc taatgtttca atagttaagg agtga                    2625
```

<210> SEQ ID NO 11
<211> LENGTH: 874
<212> TYPE: PRT
<213> ORGANISM: Artificial Sequence
<220> FEATURE:
<223> OTHER INFORMATION: translated from synthesized full length coding
       region

<400> SEQUENCE: 11

```
Met Leu Ala Arg Gln Gly Gly Ser Leu Arg Ala Ser Gln Cys Asn Ala
1               5                   10                  15

Gly Leu Ala Arg Arg Val Glu Val Gly Ala Leu Val Val Pro Arg Pro
                20                  25                  30

Ile Ser Val Asn Asp Val Val Pro His Val Tyr Ser Ala Pro Leu Ser
            35                  40                  45

Val Ala Arg Arg Ser Cys Ser Lys Ser Ser Ile Arg Ser Thr Arg Arg
        50                  55                  60

Leu Gln Thr Thr Val Cys Ser Met Val Gln Lys Trp Met Gln Arg Met
65                  70                  75                  80

Ile Ile Val Asp Asn Asn Lys Leu Asn Val Arg Ala Leu Pro Ser Phe
                85                  90                  95

Ile Asp Tyr Phe Asn Gly Ile Tyr Gly Phe Ala Thr Gly Ile Lys Asp
            100                 105                 110

Ile Met Gly Met Ile Phe Lys Thr Asp Thr Gly Gly Ser Asn Leu Thr
        115                 120                 125

Leu Asp Glu Ile Leu Lys Asn Gln Asn Leu Leu Asn Asp Ile Ser Gly
    130                 135                 140

Lys Leu Asp Gly Ile Asn Gly Asp Leu Gly Asp Leu Ile Ala Gln Gly
```

-continued

```
        145                 150                 155                 160
Asn Leu Asn Ser Glu Leu Ala Lys Glu Leu Leu Lys Ile Ser Asn Glu
                165                 170                 175
Gln Asn Gln Met Leu Asn His Val Asn Ala Gln Leu Asn Ala Ile Asn
                180                 185                 190
Ser Thr Leu Asn Ile Tyr Leu Pro Lys Ile Thr Ser Met Leu Asn Glu
                195                 200                 205
Val Met Lys Gln Asn His Val Leu Ser Leu Gln Ile Glu Phe Leu Ser
                210                 215                 220
Lys Gln Leu Gln Glu Ile Ser Asp Lys Leu Asp Ile Ile Asn Leu Asn
225                 230                 235                 240
Val Leu Ile Asn Ser Thr Leu Thr Glu Ile Thr Pro Ala Tyr Gln Arg
                245                 250                 255
Ile Lys Tyr Val Asn Glu Lys Phe Asp Glu Leu Thr Ser Thr Val Glu
                260                 265                 270
Lys Asn Pro Lys Ser Tyr Gln Asp Asn Val Thr Lys Glu Val Ile Glu
                275                 280                 285
Asn Leu Asn Glu Leu Thr Glu Leu Ala Lys Ser Val Thr Lys Asn Asp
                290                 295                 300
Met Asp Ser Phe Glu Phe Tyr Leu Gln Thr Phe His Asp Val Met Thr
305                 310                 315                 320
Gly Asn Asn Leu Phe Gly Arg Ser Ala Leu Lys Thr Ala Ser Glu Leu
                325                 330                 335
Ile Thr Lys Glu Asn Val Thr Thr Arg Gly Ser Glu Ile Gly Lys Val
                340                 345                 350
Tyr Asn Phe Leu Ile Val Leu Thr Ser Leu Gln Ala Lys Ala Phe Leu
                355                 360                 365
Thr Leu Thr Ala Cys Arg Lys Leu Leu Gly Leu Thr Asp Ile Asp Tyr
                370                 375                 380
Thr Gln Ile Met Asn His His Ile Asp Gly Gln Lys Arg Glu Phe Arg
385                 390                 395                 400
Ile Asn Ile Leu Pro Thr Leu Ser Asn Asn Phe Ser Asn Pro Ser Tyr
                405                 410                 415
Ser Lys Asn Arg Gly Ser Asp Ile Asp Asp Pro Ile Val Val Leu Glu
                420                 425                 430
Ala Ala Pro Gly Tyr Ala Leu Ile Gly Phe Glu Ile Leu Asn Asp Pro
                435                 440                 445
Leu Pro Ile Leu Lys Gly Tyr Gln Ala Arg Leu Lys Pro Asn Tyr Gln
                450                 455                 460
Val Asp Arg Glu Ser Met Ser Glu Thr Ile Tyr Gly Asp Ile His Lys
465                 470                 475                 480
Leu Phe Cys Pro Lys Gln Leu Glu Gln Lys Tyr Ile Lys Asp Ile
                485                 490                 495
Glu Phe Pro Glu Gly Tyr Val Ile Thr Lys Ile Val Phe Glu Lys Arg
                500                 505                 510
Leu Asn Gln Leu Gly Tyr Glu Val Thr Ala Asn Phe Tyr Asp Pro Ser
                515                 520                 525
Thr Gly Ser Ile Asp Leu Asn Lys Val Lys Val Glu Ser Trp Lys Glu
                530                 535                 540
Lys Ser Cys Glu Glu Asp Ser Cys Asp Glu Tyr Ser Ile Ile Lys
545                 550                 555                 560
Ala Glu Thr Asp Gly Ile Tyr Met Pro Leu Gly Val Val Ser Glu Thr
                565                 570                 575
```

Phe Leu Thr Pro Ile Tyr Gly Phe Gly Leu Thr Val Asp Glu Lys Asn
            580                 585                 590

Gln Lys Ile Thr Leu Thr Gly Lys Ser Tyr Leu Arg Glu Ser Leu Leu
        595                 600                 605

Glu Thr Asp Leu Leu Asn Asn Glu Thr Tyr Leu Ile Ala Ser Pro Asp
    610                 615                 620

Gly Tyr Ile Ser Ser Ile Val Glu Asn Trp Asn Ile Thr Ser Asp Asn
625                 630                 635                 640

Thr Gly Ser Trp Arg Ala Asn Asn Asn Ala Phe Val Asp Lys Ala
                645                 650                 655

Asp Thr Ile Lys Gly Ser Ser Leu Tyr Thr His Lys Asp Gly Glu
            660                 665                 670

Phe Ser Gln Phe Ile Gly Asn Lys Leu Lys Pro Lys Thr Asn Tyr Val
        675                 680                 685

Ile Gln Tyr Val Ile Lys Gly Arg Pro Ala Ile Tyr Leu Lys Asn Asn
    690                 695                 700

Lys Asp Thr Leu Phe Glu Asp Thr Lys Asn Asn Phe Ser Asp Phe Gln
705                 710                 715                 720

Thr Val Thr Lys Lys Phe Asn Ser Gly Val Asn Pro Ser Glu Ile Tyr
                725                 730                 735

Phe Leu Phe Lys Asn Gln Ser Glu Tyr Glu Ala Trp Gly Asn Asn Phe
            740                 745                 750

Ile Ile Leu Glu Ile Lys Ser Leu Glu Phe Leu Pro Gln Met Leu Lys
        755                 760                 765

Pro Glu Asp Trp Ile Pro Ser Gly Asn Val Gln Met Lys Asp Gly Gly
    770                 775                 780

Arg Leu Glu Ile Leu Gly Asp Gly Tyr Phe Lys Gln Phe Ile Lys Leu
785                 790                 795                 800

Glu Asn Asp Ser Thr Tyr His Leu Arg Leu Ser Val Lys Gly Thr Gly
                805                 810                 815

Arg Val Ser Ile Ile Asp Glu Ser Lys Tyr Leu Leu Phe Val Asn Val
            820                 825                 830

Lys Asp Glu Asp Leu Thr Arg Val Ile Lys Asn Thr Ser Ser Lys Gly
        835                 840                 845

Glu Cys Phe Ile Ala Leu Glu Gly Thr Tyr Val Glu Asn Ser Ser Thr
    850                 855                 860

Ile Phe Ser Asn Val Ser Ile Val Lys Glu
865                 870

<210> SEQ ID NO 12
<211> LENGTH: 2013
<212> TYPE: DNA
<213> ORGANISM: Artificial Sequence
<220> FEATURE:
<223> OTHER INFORMATION: synthesized full length coding region

<400> SEQUENCE: 12
atgttagcta gacaaggtgg atctcttaga gcttctcaat gtaacgctgg acttgctaga      60
agagttgagg ttggtgctct tgttgttcct agaccaattt ctgttaacga cgttgttcca     120
cacgtctatt ctgctcctct ttctgttgct agacgttctt gctctaagtc ctctattaga     180
agtactagaa ggcttcaaac tactgtttgc tcaatgtctt accaagataa cgttactaag     240
gaagttattg aaaaccttaa tgagcttact gagcttgcta gtctgttac aaagaacgac     300 atggattcat tcgagttcta tcttcaaact ttccatgatg ttatgactgg aataatctt     360

```
ttcgggaggt ctgcattaaa gactgcttct gaattaatca ctaaggaaaa cgtaactact        420
agaggttctg agattggaaa ggtgtataac tttcttattg ttcttacttc acttcaagct        480
aaggctttcc ttactcttac tgcttgtaga aagctccttg gtcttactga cattgattac        540
actcagatta tgaaccatca tattgatggt caaaagagag agtttaggat taatatcctt        600
ccaactcttt ctaataattt ctcaaatcca tcttactcta aaaatagagg ttctgatatt        660
gatgatccta ttgtagttct tgaagctgct cctggatacg ctcttattgg atttgagata        720
cttaacgatc cacttcctat tcttaagggt tatcaagcta gacttaaacc aaactatcaa        780
gttgatagag agtctatgtc agagactatc tacggagata ttcataaact cttttgccca        840
aagcaacttg agcaaaaata ttacattaaa gatattgaat tcctgagggg atacgtcatt        900
actaagatag tttttgaaaa agacttaat caacttggtt acgaggttac tgctaacttt         960
tacgatccat ctaccggatc tattgatctt aacaaggtta aggttgaatc ttggaaggaa       1020
aagtcttgcg aggaggattc ttgcgaagat gagtattcaa tcattaaggc tgaaacagat       1080
ggcatctata tgccacttgg agtggtttct gaaacttttc ttactcctat ctatggtttc       1140
ggacttactg ttgatgagaa gaatcaaaaa ataactttga ctgggaagtc ttatcttaga       1200
gaatctcttc ttgaaactga tcttcttaac aatgaaactt accttattgc ttctccagac       1260
ggttacattt cttctattgt tgagaactgg aatataactt ctgacaatac tggatcttgg       1320
agagctaata ataataatgc ttttgtggat aaggctgata ctataaaagg ttcttcatct       1380
ctttacactc ataaagatgg tgagtttcct caattcattg gaaacaaact taagcctaag       1440
accaattacg ttattcaata tgttataaaa gggagacctg ctatctatct taaaaataat       1500
aaagatactc ttttcgagga taccaaaaat aactttctg attttcaaac tgttactaag        1560
aaattcaatt ctggagttaa tccttctgaa atctacttcc ttttcaagaa tcaatctgaa       1620
tacgaggcat ggggaaacaa ctttatcatt ttggaaatta aatcacttga gttccttcca       1680
caaatgctta agcctgagga ttggattcct tctggaaacg ttcagatgaa agacggaggc       1740
agacttgaga ttcttggaga tggttacttt aagcaattca ttaaattgga gaatgattca       1800
acttaccatc tgagactttc tgttaaggga actggcagag tttctatcat tgatgaatct       1860
aagtatcttc tttttgtaaa tgttaaggat gaggatctga ctagagtcat taaaaatact       1920
tcttctaagg gtgagtgttt cattgctctt gagggaactt acgttgaaaa ctcttctacc       1980
attttctcta atgtttcaat agttaaggag tga                                   2013
```

<210> SEQ ID NO 13
<211> LENGTH: 670
<212> TYPE: PRT
<213> ORGANISM: Artificial Sequence
<220> FEATURE:
<223> OTHER INFORMATION: translated from synthesized full length coding region

<400> SEQUENCE: 13

```
Met Leu Ala Arg Gln Gly Gly Ser Leu Arg Ala Ser Gln Cys Asn Ala
1               5                   10                  15

Gly Leu Ala Arg Arg Val Glu Val Gly Ala Leu Val Val Pro Arg Pro
            20                  25                  30

Ile Ser Val Asn Asp Val Val Pro His Val Tyr Ser Ala Pro Leu Ser
        35                  40                  45

Val Ala Arg Arg Ser Cys Ser Lys Ser Ser Ile Arg Ser Thr Arg Arg
    50                  55                  60
```

```
Leu Gln Thr Thr Val Cys Ser Met Ser Tyr Gln Asp Asn Val Thr Lys
 65                  70                  75                  80

Glu Val Ile Glu Asn Leu Asn Glu Leu Thr Glu Leu Ala Lys Ser Val
                 85                  90                  95

Thr Lys Asn Asp Met Asp Ser Phe Glu Phe Tyr Leu Gln Thr Phe His
            100                 105                 110

Asp Val Met Thr Gly Asn Asn Leu Phe Gly Arg Ser Ala Leu Lys Thr
            115                 120                 125

Ala Ser Glu Leu Ile Thr Lys Glu Asn Val Thr Thr Arg Gly Ser Glu
130                 135                 140

Ile Gly Lys Val Tyr Asn Phe Leu Ile Val Leu Thr Ser Leu Gln Ala
145                 150                 155                 160

Lys Ala Phe Leu Thr Leu Thr Ala Cys Arg Lys Leu Leu Gly Leu Thr
                165                 170                 175

Asp Ile Asp Tyr Thr Gln Ile Met Asn His His Ile Asp Gly Gln Lys
            180                 185                 190

Arg Glu Phe Arg Ile Asn Ile Leu Pro Thr Leu Ser Asn Asn Phe Ser
            195                 200                 205

Asn Pro Ser Tyr Ser Lys Asn Arg Gly Ser Asp Ile Asp Pro Ile
210                 215                 220

Val Val Leu Glu Ala Ala Pro Gly Tyr Ala Leu Ile Gly Phe Glu Ile
225                 230                 235                 240

Leu Asn Asp Pro Leu Pro Ile Leu Lys Gly Tyr Gln Ala Arg Leu Lys
                245                 250                 255

Pro Asn Tyr Gln Val Asp Arg Glu Ser Met Ser Glu Thr Ile Tyr Gly
            260                 265                 270

Asp Ile His Lys Leu Phe Cys Pro Lys Gln Leu Glu Gln Lys Tyr Tyr
            275                 280                 285

Ile Lys Asp Ile Glu Phe Pro Glu Gly Tyr Val Ile Thr Lys Ile Val
290                 295                 300

Phe Glu Lys Arg Leu Asn Gln Leu Gly Tyr Glu Val Thr Ala Asn Phe
305                 310                 315                 320

Tyr Asp Pro Ser Thr Gly Ser Ile Asp Leu Asn Lys Val Lys Val Glu
                325                 330                 335

Ser Trp Lys Glu Lys Ser Cys Glu Glu Asp Ser Cys Glu Asp Glu Tyr
            340                 345                 350

Ser Ile Ile Lys Ala Glu Thr Asp Gly Ile Tyr Met Pro Leu Gly Val
            355                 360                 365

Val Ser Glu Thr Phe Leu Thr Pro Ile Tyr Gly Phe Gly Leu Thr Val
    370                 375                 380

Asp Glu Lys Asn Gln Lys Ile Thr Leu Thr Gly Lys Ser Tyr Leu Arg
385                 390                 395                 400

Glu Ser Leu Leu Glu Thr Asp Leu Leu Asn Asn Glu Thr Tyr Leu Ile
                405                 410                 415

Ala Ser Pro Asp Gly Tyr Ile Ser Ser Ile Val Glu Asn Trp Asn Ile
            420                 425                 430

Thr Ser Asp Asn Thr Gly Ser Trp Arg Ala Asn Asn Asn Ala Phe
            435                 440                 445

Val Asp Lys Ala Asp Thr Ile Lys Gly Ser Ser Ser Leu Tyr Thr His
    450                 455                 460

Lys Asp Gly Glu Phe Ser Gln Phe Ile Gly Asn Lys Leu Lys Pro Lys
465                 470                 475                 480
```

-continued

```
Thr Asn Tyr Val Ile Gln Tyr Val Ile Lys Gly Arg Pro Ala Ile Tyr
                485                 490                 495

Leu Lys Asn Asn Lys Asp Thr Leu Phe Glu Asp Thr Lys Asn Asn Phe
            500                 505                 510

Ser Asp Phe Gln Thr Val Thr Lys Lys Phe Asn Ser Gly Val Asn Pro
        515                 520                 525

Ser Glu Ile Tyr Phe Leu Phe Lys Asn Gln Ser Glu Tyr Glu Ala Trp
    530                 535                 540

Gly Asn Asn Phe Ile Ile Leu Glu Ile Lys Ser Leu Glu Phe Leu Pro
545                 550                 555                 560

Gln Met Leu Lys Pro Glu Asp Trp Ile Pro Ser Gly Asn Val Gln Met
                565                 570                 575

Lys Asp Gly Gly Arg Leu Glu Ile Leu Gly Asp Gly Tyr Phe Lys Gln
            580                 585                 590

Phe Ile Lys Leu Glu Asn Asp Ser Thr Tyr His Leu Arg Leu Ser Val
        595                 600                 605

Lys Gly Thr Gly Arg Val Ser Ile Ile Asp Glu Ser Lys Tyr Leu Leu
    610                 615                 620

Phe Val Asn Val Lys Asp Glu Asp Leu Thr Arg Val Ile Lys Asn Thr
625                 630                 635                 640

Ser Ser Lys Gly Glu Cys Phe Ile Ala Leu Glu Gly Thr Tyr Val Glu
                645                 650                 655

Asn Ser Ser Thr Ile Phe Ser Asn Val Ser Ile Val Lys Glu
            660                 665                 670
```

VEGETATIVE INSECTICIDAL PROTEINS USEFUL FOR CONTROL OF INSECT PESTS

CROSS-REFERENCE TO RELATED APPLICATIONS

This application is a divisional of U.S. Non-Provisional application Ser. No. 14/740,326 filed Jun. 16, 2016, which claims priority from and the benefit of U.S. Provisional Application 62/014,916, filed Jun. 20, 2014, and U.S. Non-Provisional application Ser. No. 14/740,326, filed Jun. 16, 2015. The entire contents of these applications are hereby incorporated by reference into this application.

REFERENCE TO SEQUENCE LISTING SUBMITTED ELECTRONICALLY

The official copy of the sequence listing is submitted electronically via EFS-Web as an ASCII formatted sequence listing with a file named "74948-US-DIV_20171128_Seq_Listing_DIG17_ST25", created on Nov. 28, 2017, and having a size of 53 kilobytes, and is filed concurrently with the specification. The sequence listing contained in this ASCII formatted document is part of the specification, and is incorporated herein by reference in its entirety.

FIELD OF THE INVENTION

This invention generally relates to the field of molecular biology. More specifically the invention concerns new insecticidal protein toxins developed from a new vegetative insecticidal protein toxin found in *Bacillus thuringiensis* and their use to control insects.

BACKGROUND OF INVENTION

Insects and other pests cost farmers billions of dollars annually in crop losses and expense to keep these pests under control. In addition to losses in field crops, insect pests are also a burden to vegetable and fruit growers, to producers of ornamental flowers, and to home gardeners. The losses caused by insect pests in agricultural production environments include decrease in crop yield, reduced crop quality, and increased harvesting costs.

Insect pests are mainly controlled by intensive applications of chemical pesticides, which are active through inhibition of insect growth, prevention of insect feeding or reproduction, or cause death. Good insect control can thus be reached, but these chemicals can sometimes also affect other beneficial insects. Another problem resulting from the wide use of chemical pesticides is the appearance of resistant insect populations. This has been partially alleviated by various resistance management practices, but there is an increasing need for alternative pest control agents. Biological pest control agents, such as *Bacillus thuringiensis* (Bt) strains expressing pesticidal toxins like delta-endotoxins, have also been applied to crop plants with satisfactory results, offering an alternative or compliment to chemical pesticides. The genes coding for some of these delta-endotoxins have been isolated and their expression in heterologous hosts have been shown to provide another tool for the control of economically important insect pests. In particular, the expression of insecticidal toxins, such as *Bacillus thuringiensis* delta-endotoxins, in transgenic plants have provided efficient protection against selected insect pests, and transgenic plants expressing such toxins have been commercialized, allowing farmers to reduce applications of chemical insect control agents.

The soil microbe *Bacillus thuringiensis* is a Gram-positive, spore-forming bacterium characterized by parasporal crystalline protein inclusions. *Bacillus thuringiensis* continues to be the leading source of novel insecticidal proteins for development of plant incorporated pesticides. Using various strains of bacterial isolates, we have invented new Bt toxins that are active against commercially important insect pests. In the North American maize insect resistance market, *Spodoptera frugiperda* (fall armyworm "FAW"), *Ostrinia nubialis* Hubner (European corn borer "ECB"), and *Helicoverpa zea* Boddie (corn earworm "CEW") are the key driver pests, although there are other key insect pests in other geographies (e.g. *Helicoverpa armigera* (cotton bollworm "CBW" or corn earworm "CEW")) and additional secondary, but important insect pest species. Bt toxins represent over 90% of the bioinsecticide market and essentially the entire source of genes for transgenic crops that have been developed to provide resistance to insect feeding. Bt bacteria produce insecticidal delta-endotoxins including Crystal (Cry), Cytotoxin (Cyt), and Vegetative Insecticidal Protein (VIP) toxins, depending on their gene and protein structure. Cry toxins are produced during spore formation as insoluble crystal proteins. VIP toxins, on the other hand, are produced as soluble proteins during the vegetative stage of Bt bacterial growth. VIP proteins are distinct from Cry proteins in their structure, but share the property with Cry toxins of being pore formers acting on cells located in the insect midgut (Yu, C.-G., et al., 1997 Appl. Environ. Microbiol. 63:532-536, Lee, M. K., et al., 2003, Appl. Environ. Microbiol. 69: 4648-4657, Shotkoski, F., et al., 2003, Proc. Beltwide Cotton Conf, 89-93). We describe here the invention of new VIP toxins that have broad spectrum insecticidal activity, including insecticidal activity against ECB, which is unique compared to VIP proteins currently known (Yu, C.-G., et al., 1997 Appl. Environ. Microbiol. 63:532-536).

Patent documents WO2013/134523, WO 94/21795, WO 96/10083, U.S. Pat. Nos. 5,877,012, 6,107,279, 6,137,033, and 6,291,156, as well as Estruch et al. (1996, Proc. Natl. Acad. Sci. 93:5389-5394) and Yu et al. (1997, Appl. Environ. Microbiol. 63:532-536), describe a class of insecticidal proteins called VIP3. VIP3 genes encode approximately 88 kDa proteins that are produced and secreted by *Bacillus* during its vegetative stages of growth. These toxins were reported to be distinct from crystal-forming delta-endotoxins. These documents make specific reference to toxins designated VIP1A(a), VIP1A(b), VIP2A(a), VIP2A(b), VIP3A(a), and VIP3A(b). See also Lee et al., *AEM* vol. 69, no. 8 (August 2003), pages 4648-4657, for a discussion of the mechanism of action and truncation of VIP proteins.

The VIP3A protein possesses insecticidal activity against a wide spectrum of lepidopteran pests, including FAW, CEW, *Agrotis ipsilon* Hufnagel (black cutworm "BCW"), and *Heliothis virescens* Fabricius (tobacco budworm "TBW"). More recently, VIP proteins have been found to be toxic to certain species of hemipteran insect pests (Nanasaheb, P. et al, Toxins (Basel) vol. 4, no. 6 (June 2012), pages 405-429, Sattar S. and Maiti M. K., J. Microbiol. Biotechnol. 2011, 21:937-946). Thus, the VIP class of proteins display a unique spectrum of insecticidal activities. Other disclosures, WO 98/18932, WO 98/33991, WO 98/00546, and WO 99/57282, have also now identified homologues of the VIP3 class of proteins.

The continued use of chemical and biological agents to control insect pests heightens the chance for insects to develop resistance to such control measures. Also, the high selectivity of biological control agents often results in only a few specific insect pests being controlled by each agent. Despite the success of ECB-resistant transgenic corn, the possibility of the development of resistant insect populations threatens the long-term durability of Cry proteins in ECB control and creates the need to discover and develop new Cry or other types of biological control agents to control ECB and other pests. Insect resistance to Bt Cry proteins can develop through several mechanisms (Heckel et al., 2007, Pigott and Ellar, 2007). Multiple receptor protein classes for Cry proteins have been identified within insects, and multiple examples exist within each receptor class. Resistance to a particular Cry protein may develop, for example, by means of a mutation within the toxin-binding portion of a cadherin domain of a receptor protein. A further means of resistance may be mediated through a protoxin-processing protease. Thus, resistance to Cry toxins in species of Lepidoptera has a complex genetic basis, with at least four distinct, major resistance genes. Lepidopteran insects resistant to Cry proteins have developed in the field within the species DBM (diamondback moth) (Tabashnik, 1994), *Trichoplusia ni* Hubner (cabbage looper "CL"; Janmaat and Myers 2003, 2005), and CEW (Tabashnik et al., 2008). Therefore development and deployment of new high potency plant incorporated pesticidal proteins such as those disclosed herein are both useful and needed.

Therefore, there remains a need to discover new and effective pest control agents that provide an economic benefit to farmers and that are environmentally acceptable. Particularly needed are control agents targeted to a wide spectrum of economically important insect pests that efficiently control insect populations that are, or could become, resistant to existing insect control agents and those with equal to or increased potency compared to current control agents.

BRIEF SUMMARY OF THE INVENTION

The present invention provides insecticidal VIP toxins, including the protein toxin designated herein as DIG-657 as well as variants of DIG-657, nucleic acids encoding these toxins, methods of controlling pests using the toxins, methods of producing the toxins in transgenic host cells, and transgenic plants that express the toxins. The invention further provides nucleic acid constructs comprising a nucleic acid sequence encoding an insecticidal protein selected from the group consisting of DIG-657, a DIG-657 variant, and a DIG-657 fragment. Isolated insecticidal proteins selected from the group consisting of DIG-657, a DIG-657 variant, a DIG-657 fragment and an insecticidal protein comprising residues 206 to 803 of SEQ ID NO:2 are disclosed. Also disclosed are plants, plant parts, and seeds comprising a nucleic acid sequence encoding a protein selected from the group consisting of DIG-657, a DIG-657 variant, and a DIG-657 fragment. A method for controlling an insect pest population comprising contacting individuals in said pest population with a pesticidally effective amount of a polypeptide comprising residues 206 to 803 of SEQ ID NO:2 is also disclosed.

In one embodiment the invention provides an isolated DIG-657 insect toxin polypeptide comprising a core toxin segment selected from the group consisting of (a) a polypeptide comprising the amino acid sequence of residues 206 to 803 of SEQ ID NO:2; (b) a polypeptide comprising an amino acid sequence having at least 90% sequence identity to the amino acid sequence of residues 206 to 803 of SEQ ID NO:2; (c) a polypeptide comprising an amino acid sequence of residues 206 to 803 of SEQ ID NO:2 with up to 20 amino acid substitutions, deletions, or modifications that do not adversely affect expression or activity of the toxin encoded by SEQ ID NO:2; or an insecticidally active fragment thereof.

In another embodiment the invention provides an isolated DIG-657 insect toxin polypeptide comprising a DIG-657 core toxin segment selected from the group consisting of (a) a polypeptide comprising the amino acid sequence of residues 1 to 803 of SEQ ID NO:2; (b) a polypeptide comprising an amino acid sequence having at least 95% or 96% or 97% or 98% or 99% sequence identity to the amino acid sequence of residues 1 to 803 of SEQ ID NO:2; (c) a polypeptide comprising an amino acid sequence of residues 1 to 803 of SEQ ID NO:2 with up to 20 amino acid substitutions, deletions, or modifications that do not adversely affect expression or activity of the toxin encoded by SEQ ID NO:1; or an insecticidally active fragment thereof; (d) a polypeptide comprising an amino acid sequence having at least 93% or 94% or 95% or 96% or 97% or 98% or 99% sequence identity to the amino acid sequence of residues 206 to 803 of SEQ ID NO:2 that do not adversely affect expression or toxin activity.

In another embodiment the invention provides fertile plants comprising a DIG-657 insect toxin. The present invention further provides a method of producing an insect-resistant or insect tolerant transgenic plant, comprising introducing a nucleic acid molecule of the invention into the transgenic plant, wherein the nucleic acid molecule is expressible in the transgenic plant in an effective amount to control insects.

In another embodiment the invention provides a method for controlling a pest population comprising contacting said population with a pesticidally effective amount of a DIG-657 insect toxin.

In another embodiment the invention provides isolated nucleic acid molecules that encode a DIG-657 toxin of the invention. Given an amino acid sequences for DIG-657 toxins, coding sequences can be designed by reverse translating the amino acid sequence using codons preferred by the intended host plant, and then refining sequences using alternative codons to remove sequences that might cause problems and provide periodic stop codons to eliminate long open coding sequences in the non-coding reading frames.

In another embodiment the invention provides DNA constructs comprising a nucleotide sequence that encodes a DIG-657 insect toxin operably linked to a promoter that is not derived from Bt and is capable of driving expression in a plant. The invention also provides a transgenic plant that comprises the DNA construct stably incorporated into its genome and a method for protecting a plant from a pest comprising introducing the construct into said plant.

In yet another embodiment, the invention provides a method for producing an insect resistant or insect tolerant plant comprising breeding a non transgenic plant with a transgenic plant comprising a foreign DNA construct, capable of expressing a DIG-657 toxin, stably incorporated into the genome of the plant and selecting progeny by analyzing for at least a portion of the foreign DNA construct emanating from the transgenic plant.

DESCRIPTION OF THE DRAWING

FIG. 1 is an image of an SDS-PAGE of purified DIG-657. Lane 1, molecular weight marker; lane 2, 3 µg purified full length DIG-657; lane 3, reaction products of DIG-657 after the purified full length protein is treated with trypsin (1:10 DIG-657 wt/trypsin wt) for 1 hr.

DESCRIPTION OF THE SEQUENCES

SEQ ID NO:1 DNA sequence encoding full-length DIG-657 insect toxin.
SEQ ID NO:2 The deduced DIG-657 protein sequence.
SEQ ID NO:3 Maize-optimized DNA sequence encoding DIG-657 variant 1.
SEQ ID NO:4 DIG-657 variant 2 with codons optimized for expression in *Pseudomonas fluorescens*.
SEQ ID NO:5 DIG-657 v4, Maize optimized High GC content.
SEQ ID NO:6 DIG-657 v5 Maize optimized High GC content of DIG-657 truncated 205 AA from the N-terminal.
SEQ ID NO:7 The deduced protein sequence of SEQ ID NO:6.
SEQ ID NO:8 The full length DIG-657 soybean most preferred codon optimized version.
SEQ ID NO:9 The soybean most preferred codon optimized version of truncated DIG-657.
SEQ ID NO:10 DNA encoding chloroplast transit peptide 4 (Trap4) fused to the soybean most preferred codon optimized version of full length DIG-657.
SEQ ID NO:11 Deduced protein sequence of TraP4 DIG-657 full length soybean most preferred codon.
SEQ ID NO:12 Trap 4 fused to the soybean most preferred codon optimized version of truncated DIG-657.
SEQ ID NO:13 Deduced protein sequence of Trap4 DIG-657 truncated version.

DETAILED DESCRIPTION OF THE INVENTION

The present invention provides insecticidal protein toxins and methods for delivering the toxins that are functionally active and effective against many orders of insects, preferably Lepidopteran insects. By "functional activity" (or "active against") it is meant that the proteins function as orally active toxin or insect control agents, that the proteins have a toxic effect, or are able to disrupt or deter insect growth or feeding. When an insect comes into contact with an effective amount of a toxin of the subject invention delivered via transgenic plant expression, formulated protein composition(s), sprayable protein composition(s), a bait matrix or other delivery system, the results are typically death of the insect, inhibition of the growth or proliferation of the insect, or prevention of the insects from feeding upon the source, preferably a transgenic plant, that makes the toxins available to the insects. Functional proteins of the subject invention can also work together or alone to enhance or improve the activity of one or more other toxin proteins. The terms "toxic," "toxicity," or "toxin" are meant to convey that the subject toxins have functional activity as defined herein.

Complete lethality to feeding insects is preferred but is not required to achieve functional activity. If an insect avoids the toxin or ceases feeding, that avoidance will be useful in some applications, even if the effects are sublethal or lethality is delayed or indirect. For example, if insect resistant transgenic plants are desired, the reluctance of insects to feed on the plants is as useful as lethal toxicity to the insects because the ultimate objective is avoiding insect-induced plant damage.

A nucleic acid encoding DIG-657 was discovered and isolated from Bt strain PS46L. By "isolated" applicants mean that the nucleic acid molecules have been removed from their native environment and have been placed in a different environment by the hand of man. Because of the redundancy of the genetic code, a variety of different DNA sequences can encode the amino acid sequences disclosed herein. It is well within the skill of a person trained in the art to create these alternative DNA sequences encoding the same, or essentially the same, toxins once the amino acid sequences are known. The nucleic acid sequence for the full length coding region of DIG-657 (SEQ ID NO:1) was determined, and the full length protein sequence of DIG-657 (SEQ ID NO:2) was deduced from the nucleic acid sequence. The DIG-657 protein sequence was queried against the GenomeQuest databases "GQ-Pat Platinum protein" and "GQ-Pat GoldPlus protein", as well as the GenBank non-redundant protein database. The closest known homologs are XMI335 (94% identity, WO2013134523-002) and Vip3Ba (74% identity, Accession No. AAV70653, Rang et al).

Insect active variants of the DIG-657 toxin are also described herein, and are referred to collectively as DIG-657 insect toxins, or variants and include fragments and truncated forms. Individual variants of DIG-657 may be identified by specific DIG-nomenclature. DIG-657 toxins are ideal candidates for use to control Lepidopteran pests.

A surprising property of DIG-657 and its variant toxins is that they were found to be active against populations of ECB and DBM that are resistant to Cry1F and Cry1A toxins. Accordingly, DIG-657 toxins are ideal candidates for control and prevention of resistant Lepidopteran pest populations.

The DIG-657 toxins of the invention are active against Lepidopteran insects, preferably against DBM, ECB, FAW, CEW, CBW, and TBW. Insecticidal activity is also expected for BCW, CL, *Spodoptera exigua* (beet armyworm "BAW"), *Pectinophora gossypiella* (pink bollworm), *Cochyles hospes* Walsingham (banded sunflower moth), and *Homoeosoma electellum* (sunflower head moth).

Insecticidal activity of DIG-657 produced in *Pseudomonas fluorescens* was demonstrated to be active on Lepidopteran species including ECB; cry1F-resistant ECB (rECB), DBM, cry1A-resistant DBM (rDBM), CEW, BCW, and TBW. DIG-657 protein was also tested for activity on CBW, FAW and Cry1F-resistant FAW (rFAW).

This spectrum of biological activity against both insect pests of maize and soybean is highly advantageous. The trypsin truncated toxin (SEQ ID NO:7) was tested against ECB in bioassay and shown to be approximately equal in activity to the full length DIG-657, indicating that the first 205 amino acids on the N-terminus of the protein are not required for biological activity.

Full length DIG-657 has an intact N-terminus and when treated with trypsin (1:10 trypsin/DIG-657), the protein is cleaved to two bands, one at approximately 65 kDa and another one at about 18 kDa (FIG. 1). In addition, a small residual full length DIG-657 was also present. N-terminal amino acid analysis of the 65 kDa cleaved product of DIG-657 indicated that the site of trypsin cleavage is (205K/S206).

Nucleotide sequences that encode DIG-657, its variants, truncations and fragments, may be synthesized and cloned into standard plasmid vectors by conventional means, or may be obtained by standard molecular biology manipulation of other constructs containing the nucleotide sequences. Unique restriction sites internal to a DIG-657 coding region may be identified and DNA fragments comprising the sequences between the restriction sites of the DIG-657 coding region may be synthesized, each such fragment encoding a specific deletion, insertion or other DIG-657 variation. The DNA fragments encoding the modified DIG-657 fragments may be joined to other DIG-657 coding region fragments or other Cry or VIP coding region fragments at appropriate restriction sites to obtain a coding region encoding the desired full-length DIG-657 protein, deleted or variant DIG-657 protein. For example, one may identify an appropriate restriction recognition site at the start of a first DIG-657 coding region, and a second restriction site internal to the DIG-657 coding region. Cleavage of this first DIG-657 coding region at these restriction sites would generate a DNA fragment comprising part of the first DIG-657 coding region. A second DNA fragment flanked by analogously-situated compatible restriction sites specific for another DIG-657 coding region or other VIP3 coding region may be used in combination with the first DNA restriction fragment to construct a variant.

Anti-toxin antibodies. Antibodies to the toxins disclosed herein, or fragments of these toxins, can be prepared using standard procedures well known in the art. Such antibodies are useful to detect the presence of DIG-657 toxins in plant tissues and a variety of other substances. Such antibodies and anti-sera are useful in various methods of detecting the claimed DIG-657 toxins of the invention, and variants or fragments thereof. It is well known that antibodies labeled with a reporting group can be used to identify the presence of antigens in a variety of milieus. Antibodies labeled with radioisotopes have been used in radioimmuno assays to identify, with great precision and sensitivity, the presence of antigens in a variety of biological fluids. More recently, enzyme labeled antibodies have been used as a substitute for radiolabeled antibodies in the ELISA assay. Further, antibodies immunoreactive to the Bt insecticidal toxin of the present invention can be bound to an immobilizing substance such as a polystyrene well or particle and used in immunoassays to determine whether the Bt toxin is present in a test sample. Anti-DIG-657 antibodies are also used for isolating quantities of DIG-657 toxins from recombinant production systems or natural sources.

Transgenic Expression of DIG-657. The subject protein toxins can be "applied" or provided to contact the target insects in a variety of ways. For example, DIG-657 toxins can be used as plant-incorporated protectants in transgenic plants (produced by and present in the plant) and are well-known in the art. Expression of the toxin genes can also achieve selectivity in specific tissues of the plants, such as the roots, leaves, etc. This can be accomplished via the use of tissue-specific promoters well known in the art.

A preferred embodiment of the subject invention is the transformation of plants with genes encoding the subject insecticidal protein or its variants. The transformed plants are resistant to attack by an insect target pest by virtue of the presence of controlling amounts of the subject insecticidal protein or its variants in the cells of the transformed plant. By incorporating and expressing genetic material that encodes a DIG-657 toxin into the genome of a plant eaten by a particular insect pest, the adult or larvae will die after consuming the food plant. Numerous members of the monocotyledonous and dicotyledonous classifications have been transformed. Transgenic agronomic crops as well as fruits and vegetables are of commercial interest. Such crops include, but are not limited to, maize, rice, soybeans, canola, sunflower, alfalfa, sorghum, wheat, cotton, peanuts, tomatoes, potatoes, and the like. Numerous well known techniques exist for introducing foreign genetic material into monocot or dicot plant cells, and for obtaining fertile plants that stably maintain and express the introduced gene.

In one preferred embodiment, DIG-657 or a variant is delivered orally through a transgenic plant comprising a nucleic acid sequence that expresses a toxin of the present invention. The present invention provides a method of producing an insect-resistant transgenic plant, comprising introducing a nucleic acid molecule of the invention into the plant wherein the toxin is expressible in the transgenic plant in an effective amount to control an insect. In a non-limiting example, a basic cloning strategy may be to subclone full length or modified DIG-657 coding sequences into a plant expression plasmid at Nco1 and Sac1 restriction sites. The resulting plant expression cassettes containing the appropriate DIG-657 coding region under the control of plant expression elements, (e.g., plant expressible promoters, 3' terminal transcription termination and polyadenylate addition determinants, and the like) are subcloned into a binary vector plasmid, utilizing, for example, Gateway® technology or standard restriction enzyme fragment cloning procedures. LR Clonase™ (Invitrogen, Carlsbad, Calif.) for example, may be used to recombine the full length and modified gene plant expression cassettes into a binary plant transformation plasmid if the Gateway® technology is utilized. It is convenient to employ a binary plant transformation vector that harbors a bacterial gene that confers resistance to the antibiotic spectinomycin when the plasmid is present in *E. coli* and *Agrobacterium* cells. It is also convenient to employ a binary vector plasmid that contains a plant-expressible selectable marker gene that is functional in the desired host plants. Examples of plant-expressible selectable marker genes include but are not limited to those that encode the aminoglycoside phosphotransferase gene (aphII) of transposon Tn5, which confers resistance to the antibiotics kanamycin, neomycin and G418, as well as those genes which code for resistance or tolerance to glyphosate; hygromycin; methotrexate; phosphinothricin (bialaphos), imidazolinones, sulfonylureas and triazolopyrimidine herbicides, such as chlorosulfuron, bromoxynil, dalapon and the like.

Alternatively, the plasmid structure of the binary plant transformation vector containing the DIG-657 gene insert is performed by restriction digest fingerprint mapping of plasmid DNA prepared from candidate *Agrobacterium* isolates by standard molecular biology methods well known to those skilled in the art of *Agrobacterium* manipulation.

Those skilled in the art of obtaining transformed plants via *Agrobacterium*-mediated transformation methods will understand that other *Agrobacterium* strains besides Z707S may be used, and the choice of strain may depend upon the identity of the host plant species to be transformed.

Insect Bioassays of transgenic *Arabidopsis*. Transgenic *Arabidopsis* lines expressing modified DIG-657 proteins can be used to demonstrate activity against sensitive insect species in artificial diet overlay assays. Protein extracted from transgenic and non-transgenic *Arabidopsis* lines may be quantified by appropriate methods and sample volumes adjusted to normalize protein concentration. Bioassays are then conducted on artificial diet as described below. Non-transgenic *Arabidopsis* and/or buffer and water should be included in assays as background check treatments.

Bioassay of transgenic maize. Bioactivity of the DIG-657 toxins and variants produced in plant cells also may be demonstrated by conventional bioassay methods (see, for example Huang et al., 2006). Efficacy may be tested by feeding various plant tissues or tissue pieces derived from a plant producing a DIG-657 toxin to target insects in a controlled feeding environment. Alternatively, protein extracts may be prepared from various plant tissues derived from a plant producing the DIG-657 toxin and incorporate the extracted proteins in an artificial diet bioassay. It is to be understood that the results of such feeding assays are to be compared to similarly conducted bioassays that employ appropriate control tissues from host plants that do not produce the DIG-657 protein or variants, or to other control samples.

DIG-657 toxins, and insecticidally active variants. In addition to the full length DIG-657 toxin of SEQ ID NO:2, the invention encompasses insecticidally active variants of SEQ ID NO:2, SEQ ID NO:11, or SEQ ID NO:13. By the term variant, applicants intend to include certain deletion, substitution, and insertion mutants. A DIG-657 fragment is any protein sequence that is found in SEQ ID NO:2 that is less than the full length DIG-657 amino acid sequence and which has insecticidal properties. DIG-657 variant fragments are also contemplated as part of the invention and are defined as fragments of DIG-657 containing certain deletion, substitution, and insertion mutants described herein and which have insecticidal activity. As a preface to describing variants of the DIG-657 toxins that are included in the invention, it will be useful to briefly review the architecture of DIG-657 protein toxins.

DIG-657 variants created by making a limited number of amino acid deletions, substitutions, or additions. Amino acid deletions, substitutions, and additions to the amino acid sequence of SEQ ID NO:2 can readily be made in a sequential manner and the effects of such variations on insecticidal activity can be tested by bioassay. Provided the number of changes is limited in number, such testing does not involve unreasonable experimentation. The invention also includes insecticidally active variants of the core toxin segment (amino acids 206-803 of SEQ ID NO:2, or in which up to 10, up to 15, or up to 20 independent amino acid additions, deletions, or substitutions have been made).

Variants may be made by making random mutations or the variants may be designed. In the case of designed mutants, there is a high probability of generating variants with similar activity to the native toxin when amino acid identity is maintained in critical regions of the toxin which account for biological activity or are involved in the determination of three-dimensional configuration which ultimately is responsible for the biological activity. A high probability of retaining activity will also occur if substitutions are conservative. Amino acids may be placed in the following classes: nonpolar, uncharged polar, basic, and acidic. Conservative substitutions whereby an amino acid of one class is replaced with another amino acid of the same type are least likely to materially alter the biological activity of the variant. Table 1 provides a listing of examples of amino acids belonging to each class.

TABLE 1

| Class of Amino Acid | Examples of Amino Acids |
|---|---|
| Nonpolar Side Chains | Ala (A), Val (V), Leu (L), Ile (I), Pro (P), Met (M), Phe (F), Trp (W) |
| Uncharged Polar Side Chains | Gly (G), Ser (S), Thr (T), Cys (C), Tyr (Y), Asn (N), Gln (Q) |
| Acidic Side Chains | Asp (D), Glu (E) |
| Basic Side Chains | Lys (K), Arg (R), His (H) |
| Beta-branched Side Chains | Thr, Val, Ile |
| Aromatic Side Chains | Tyr, Phe, Trp, His |

Pesticidal proteins of the present invention are encoded by a nucleotide sequence sufficiently identical to the nucleotide sequence of SEQ ID NO:1, or the pesticidal proteins are sufficiently identical to the amino acid sequence set forth in SEQ ID NO:2. By "sufficiently identical" is intended an amino acid or nucleotide sequence that has at least about 60% or 65% sequence identity, about 70% or 75% sequence identity, about 80% or 85% sequence identity, about 90%, 91%, 92%, 93%, 94%, 95%, 96%, 97%, 98%, 99% or greater sequence identity compared to a reference sequence using one of the alignment programs described herein using standard parameters. One of skill in the art will recognize that these values can be appropriately adjusted to determine corresponding identity of proteins encoded by two nucleotide sequences by taking into account codon degeneracy, amino acid similarity, reading frame positioning, and the like.

To determine the percent identity of two amino acid sequences or of two nucleic acids, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are the same length. In another embodiment, the percent identity is calculated across the entirety of the reference sequence. The percent identity between two sequences can be determined using techniques similar to those described below, with or without allowing gaps. In calculating percent identity, typically exact matches are counted. A gap, (a position in an alignment where a residue is present in one sequence but not in the other) is regarded as a position with non-identical residues.

The determination of percent identity between two sequences can be accomplished using a mathematical algorithm. A non-limiting example of a mathematical algorithm utilized for the comparison of two sequences is the algorithm of Karlin and Altschul (1990) *Proc. Nat'l. Acad. Sci. USA* 87:2264, modified as in Karlin and Altschul (1993) *Proc. Nat'l. Acad. Sci. USA* 90:5873-5877. Such an algorithm is incorporated into the BLASTN and BLASTX programs of Altschul et al. (1990) *J. Mol. Biol.* 215:403. BLAST nucleotide searches can be performed with the BLASTN program, score=100, word length=12, to obtain nucleotide sequences homologous to pesticidal-like nucleic acid molecules of the invention. BLAST protein searches can be performed with the BLASTX program, score=50, word length=3, to obtain amino acid sequences homologous to pesticidal protein molecules of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., BLASTX and BLASTN) can be used. Alignment may also be performed manually by inspection.

Another non-limiting example of a mathematical algorithm utilized for the comparison of sequences is the ClustalW algorithm (Higgins et al. (1994) *Nucleic Acids Res.* 22:4673-4680). ClustalW compares sequences and aligns the entirety of the amino acid or DNA sequence, and thus can provide data about the sequence conservation of the entire amino acid sequence. The ClustalW algorithm is used in several commercially available DNA/amino acid analysis software packages, such as the ALIGNX module of the Vector NTI Program Suite (Invitrogen Corporation, Carlsbad, Calif.). After alignment of amino acid sequences with ClustalW, the percent amino acid identity can be assessed. A non-limiting example of a software program useful for analysis of ClustalW alignments is GENEDOC™. GENEDOC™ (Karl Nicholas) allows assessment of amino acid (or DNA) similarity and identity between multiple proteins. Another non-limiting example of a mathematical algorithm utilized for the comparison of sequences is the algorithm of Myers and Miller (1988) *CABIOS* 4(1):11-17. Such an algorithm is incorporated into the ALIGN program (version 2.0), which is part of the GCG Wisconsin Genetics Software Package, Version 10 (available from Accelrys, Inc., San Diego, Calif., USA). When utilizing the ALIGN program for comparing amino acid sequences, a PAM120 weight residue table, a gap length penalty of 12, and a gap penalty of 4 can be used. Unless otherwise stated, GAP Version 10, which uses the algorithm of Needleman and Wunsch (1970) *J. Mol. Biol.* 48(3):443-453, will be used to determine sequence identity or similarity using the following parameters: % identity and % similarity for a nucleotide sequence using GAP Weight of 50 and Length Weight of 3, and the nwsgapdna.cmp scoring matrix; % identity or % similarity for an amino acid sequence using GAP weight of 8 and length weight of 2, and the BLOSUM62 scoring program. Equivalent programs may also be used. By "equivalent program" is intended any sequence comparison program that, for any two sequences in question, generates an alignment having identical nucleotide residue matches and an identical percent sequence identity when compared to the corresponding alignment generated by GAP Version 10.

Protease sensitivity variants. VIP3 proteins, including DIG-657, may be proteolytically truncated from about 88 kDa in size to a product of about 66 kDa in size. The 66 kDa protein comprises amino acid residues 206-803. Insect gut proteases typically function in aiding the insect in obtaining needed amino acids from dietary protein. The best understood insect digestive proteases are serine proteases, which appear to be the most common type (Englemann and Geraerts (1980), particularly in Lepidopteran species. Coleopteran insects have guts that are more neutral to acidic than are Lepidopteran guts. The majority of Coleopteran larvae and adults, for example Colorado potato beetle (CPB), have slightly acidic midguts, and cysteine proteases provide the major proteolytic activity (Wolfson and Murdock, 1990). More precisely, Thie and Houseman (1990) identified and characterized the cysteine proteases, cathepsin B-like and cathepsin H-like, and the aspartyl protease, cathepsin D-like, in CPB. Gillikin et al. (1992) characterized the proteolytic activity in the guts of WCR larvae and found primarily cysteine proteases. U.S. Pat. No. 7,230,167 disclosed that a protease activity attributed to cathepsin G exists in WCR. The diversity and different activity levels of the insect gut proteases may influence an insect's sensitivity to a particular Bt toxin.

In another embodiment of the invention, protease cleavage sites may be engineered at desired locations to affect protein processing within the midgut of susceptible larvae of certain insect pests. These protease cleavage sites may be introduced by methods such as chemical gene synthesis or splice overlap PCR (Horton et al., 1989). Serine protease recognition sequences, for example, can optionally be inserted at specific sites in the Cry protein structure to affect protein processing at desired deletion points within the midgut of susceptible larvae. Serine proteases that can be exploited in such fashion include Lepidopteran midgut serine proteases such as trypsin or trypsin-like enzymes, chymotrypsin, elastase, etc. (Christeller et al., 1992). Further, deletion sites identified empirically by sequencing Cry protein digestion products generated with unfractionated larval midgut protease preparations or by binding to brush border membrane vesicles can be engineered to effect protein activation. Modified Cry or VIP3 proteins generated either by gene deletion or by introduction of protease cleavage sites having improved activity on Lepidopteran pests including ECB, CEW, CBW, BCW, FAW, BAW, *Diatraea grandiosella, Diatraea saccharalis, Loxagrotis albicosta*, and other target pests.

Lepidopteran and Coleopteran serine proteases such as trypsin, chymotrypsin and cathepsin G-like protease, Lepidopteran and Coleopteran cysteine proteases such as cathepsins (B-like, L-like, O-like, and K-like proteases) (Koiwa et al., (2000) and Bown et al., (2004)), Lepidopteran and Coleopteran metalloproteases such as ADAM10 (Ochoa-Campuzano et al., (2007)), and Lepidoperan and Coleopteran aspartic acid proteases such as cathepsins D-like and E-like, pepsin, plasmepsin, and chymosin may further be exploited by engineering appropriate recognition sequences at desired processing sites to affect Cry protein processing within the midgut of susceptible larvae of certain insect pests and perhaps also function to provide activity against non-susceptible insect pests.

DIG-657 variants produced by introduction or elimination of protease processing sites at appropriate positions in the coding sequence to allow, or eliminate, proteolytic cleavage of a larger variant protein by insect, plant, or microorganism proteases are within the scope of the invention. The end result of such manipulation is understood to be the generation of toxin fragment molecules having the same or better activity as the intact (full length) toxin protein.

Spray-on applications are another example and are also known in the art. The subject proteins can be appropriately formulated for the desired end use, and then sprayed (or otherwise applied) onto the plant and/or around the plant and/or to the vicinity of the plant to be protected—before an infestation is discovered, after target insects are discovered, both before and after, and the like. Bait granules, for example, can also be used and are known in the art.

When an insect comes into contact with an effective amount of toxin delivered via transgenic plant expression, formulated protein composition(s), sprayable protein composition(s), a bait matrix or other delivery system, the results are typically death of the insect, or the insects do not feed upon the source which makes the toxins available to the insects.

With suitable microbial hosts, e.g. Pseudomonas, the microbes can be applied to the environment of the pest, where they will proliferate and be ingested. The result is control of the pest. Alternatively, the microbe hosting the toxin gene can be treated under conditions that prolong the activity of the toxin and stabilize the cell. The treated cell, which retains the toxic activity, then can be applied to the environment of the target pest.

Development of Oligonucleotide Probes. A further method for identifying the toxins and genes of the subject invention is through the use of oligonucleotide probes. These probes are detectable nucleotide sequences. These sequences may be rendered detectable by virtue of an appropriate radioactive label or may be made inherently fluorescent as described in, for example, U.S. Pat. No. 6,268,132. As is well known in the art, if the probe molecule and nucleic acid sample hybridize by forming strong base-pairing bonds between the two molecules, it can be reasonably assumed that the probe and sample have substantial sequence homology. Preferably, hybridization is conducted under stringent conditions by techniques well-known in the art, as described, for example, in Keller and Manak (1993). Detection of the probe provides a means for determining in a known manner whether hybridization has occurred. Such a probe analysis provides a rapid method for identifying toxin-encoding genes of the subject invention. The nucleotide segments which are used as probes according to the invention can be synthesized using a DNA synthesizer and standard procedures. These nucleotide sequences can also be used as PCR primers to amplify genes of the subject invention.

Nucleic acid hybridization. As is well known to those skilled in molecular biology, similarity of two nucleic acids can be characterized by their tendency to hybridize. As used herein the terms "stringent conditions" or "stringent hybridization conditions" are intended to refer to conditions under which a probe will hybridize (anneal) to its target sequence to a detectably greater degree than to other sequences (e.g. at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to pH 8.3 and the temperature is at least about 30° C. for short probes (e.g. 10 to 50 nucleotides) and at least about 60° C. for long probes (e.g. greater than 50 nucleotides). Stringent conditions may also be achieved with the addition of destabilizing agents such as formamide. Exemplary low stringency conditions include hybridization with a buffer solution of 30% to 35% formamide, 1 M NaCl, 1% SDS (sodium dodecyl sulfate) at 37° C. and a wash in 1× to 2×SSC (20×SSC=3.0 M NaCl/0.3 M trisodium citrate) at 50° C. to 55° C. Exemplary moderate stringency conditions include hybridization in 40% to 45% formamide, 1.0 M NaCl, 1% SDS at 37° C. and a wash in 0.5× to 1×SSC at 55° C. to 60° C. Exemplary high stringency conditions include hybridization in 50% formamide, 1 M NaCl, 1% SDS at 37° C. and a wash in 0.1×SSC at 60° C. to 65° C. Optionally, wash buffers may comprise about 0.1% to about 1% SDS. Duration of hybridization is generally less than about 24 hours, usually about 4 to 12 hours.

Specificity is typically the function of post-hybridization washes, the critical factors being the ionic strength and temperature of the final wash solution. For DNA/DNA hybrids, the thermal melting point ($T_m$) is the temperature (under defined ionic strength and pH) at which 50% of a complementary target sequence hybridizes to a perfectly matched probe. $T_m$ is reduced by about 1° C. for each 1% of mismatching; thus, $T_m$, hybridization conditions, and/or wash conditions can be adjusted to facilitate annealing of sequences of the desired identity. For example, if sequences with >90% identity are sought, the $T_m$ can be decreased 10° C. Generally, stringent conditions are selected to be about 5° C. lower than the $T_m$ for the specific sequence and its complement at a defined ionic strength and pH. However, highly stringent conditions can utilize a hybridization and/or wash at 1° C., 2° C., 3° C., or 4° C. lower than the $T_m$; moderately stringent conditions can utilize a hybridization and/or wash at 6° C., 7° C., 8° C., 9° C., or 10° C. lower than the $T_m$, and low stringency conditions can utilize a hybridization and/or wash at 11° C., 12° C., 13° C., 14° C., 15° C., or 20° C. lower than the $T_m$.

$T_m$ (in ° C.) may be experimentally determined or may be approximated by calculation. For DNA-DNA hybrids, the $T_m$ can be approximated from the equation of Meinkoth and Wahl (1984): $T_m$(° C.)=81.5° C.+16.6(log M)+0.41(% GC)−0.61(% formamide)−500/L; where M is the molarity of monovalent cations, % GC is the percentage of guanosine and cytosine nucleotides in the DNA, % formamide is the percentage of formamide in the hybridization solution, and L is the length of the hybrid in base pairs. Alternatively, the $T_m$ is described by the following formula (Beltz et al., 1983): $T_m$(° C.)=81.5° C.+16.6(log[Na+])+0.41(% GC)−0.61(% formamide)−600/L where [Na+] is the molarity of sodium ions, % GC is the percentage of guanosine and cytosine nucleotides in the DNA, % formamide is the percentage of formamide in the hybridization solution, and L is the length of the hybrid in base pairs.

Using the equations, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Hybridization with Nucleic Acid Probes Vol. 1 by P. Tijssen (1993, ISBN-10: 0444898840, ISBN-13: 9780444898845 Hardcover) and Ausubel et al. (1995). Also see Sambrook et al. (1989).

EXAMPLES

Example 1

Construction of expression plasmids encoding DIG-657 insecticidal toxin and expression in bacterial hosts. Standard cloning methods were used in the construction of *Pseudomonas fluorescens* (Pf) expression plasmids engineered to produce full-length DIG-657 proteins encoded by plant-optimized coding regions. Restriction endonucleases and T4 DNA Ligase were obtained from New England BioLabs (NEB; Ipswich, Mass.) for restriction digestion and DNA ligation, respectively. Plasmid preparations were performed using the NucleoSpin® Plasmid Kit (Macherey-Nagel Inc, Bethlehem, Pa.) following the instructions of the suppliers for low-copy plasmid purification. DNA fragments were purified using a QIAquick® Gel Extraction Kit (Qiagen, Venio, Limburg) after agarose Tris-acetate gel electrophoresis.

The gene encoding DIG-657 was amplified out of the parental Bt Strain PS46L/DBt11889 using gene specific primers containing specific restriction sites for cloning. The resulting DIG-657 Polymerase Chain Reaction (PCR) product was then cloned into *Pseudomonas fluorescens* expression vector pDOW1169 using the traditional ligation cloning method.

The basic cloning strategy entailed subcloning the DIG-657 toxin coding sequence (CDS) (SEQ ID NO:1) into pDOW1169 at the Spe1 and Sal1 restriction sites, whereby it is placed under the expression control of the Ptac promoter and the rrnBT1T2 terminator from plasmid pKK223-3 (PL Pharmacia, Milwaukee, Wis.). pDOW1169 is a medium copy plasmid with the RSF1010 origin of replication, a pyrF gene, and a ribosome binding site preceding the restriction enzyme recognition sites into which DNA fragments containing protein coding regions may be introduced, (US Application 20080193974). The expression plasmid, designated pDOW1169, was transformed by electroporation into DC454 (a near wild-type *P. fluorescens* strain having mutations deltapyrF and lsc::lacI$^{QI}$), or its derivatives, recovered in SOC-Soy hydrolysate medium, and plated on selective medium (M9 glucose agar lacking uracil, Sambrook et al., supra). Details of the microbiological manipulations are available in Squires et al., (2004), US Patent Application 20060008877, US Patent Application 20080193974, and US Patent Application 20080058262, incorporated herein by reference. Colonies were first screened by restriction digestion of miniprep plasmid DNA. Plasmid DNA of selected clones containing DIG-657 toxin were digested with four restriction enzymes and sequence verified to further validate presence of the insert.

Example 2

Growth and Expression Analysis in Shake Flasks. Production of DIG-657 toxin for characterization and insect bioassay was accomplished by shake-flask-grown *P. fluorescens* strains harboring expression constructs (pDOW1169). A glycerol stock of DIG-657 culture (0.5 mL) was inoculated into 50 mL of defined production medium with 9.5% glycerol (Teknova Catalog No. 3D7426, Hollister, Calif.). Expression of the DIG-657 toxin gene via the Ptac promoter was induced by addition of isopropyl-β-D-1-thiogalactopyranoside (IPTG) after an initial incubation of 24 hours at 30° C. with shaking. Cultures were sampled at the time of induction and at various times post-induction. Cell density was measured by optical density at 600 nm ($OD_{600}$). Other culture media suitable for growth of *Pseudomonas fluorescens* may also be utilized, for example, as described in Huang et al. (2007) and US Patent Application 20060008877.

Example 3

*Agrobacterium* transformation. Standard cloning methods were used in the construction of binary plant transformation and expression plasmids. Restriction endonucleases and T4 DNA Ligase were obtained from NEB. Plasmid preparations were performed using the NucleoSpin® Plasmid Preparation kit or the NucleoBond® AX Xtra Midi kit (both from Macherey-Nagel, Duren, Germany), following the instructions of the manufacturers. DNA fragments were purified using the QIAquick® PCR Purification Kit or the QIAEX II® Gel Extraction Kit (both from Qiagen Venio, Limburg) after gel isolation.

Electro-competent cells of *Agrobacterium tumefaciens* strain Z7075 (a streptomycin-resistant derivative of Z707; Hepburn et al., 1985) were prepared and transformed using electroporation (Weigel and Glazebrook, 2002). After electroporation, 1 mL of Yeast Extract Peptone (YEP) broth (10 gm/L yeast extract, 10 gm/L peptone, and 5 gm/L NaCl) was added to the cuvette and the cell-YEP suspension was transferred to a 15 mL culture tube for incubation at 28° C. in a water bath with constant agitation for 4 hours. The cells were plated on YEP plus agar (25 gm/L) with spectinomycin (200 μg/mL) and streptomycin (250 μg/mL) and the plates were incubated for 2-4 days at 28° C. Well separated single colonies were selected and streaked onto fresh YEP+agar plates with spectinomycin and streptomycin as described above, and incubated at 28° C. for 1-3 days.

The presence of the DIG-657 gene insert in the binary plant transformation vector was performed by PCR analysis using vector-specific primers with template plasmid DNA prepared from selected *Agrobacterium* colonies. The cell pellet from a 4 mL aliquot of a 15 mL overnight culture grown in YEP with spectinomycin and streptomycin as before was extracted using Qiagen (Venlo, Limburg, Netherlands) Spin® Mini Preps, performed per manufacturer's instructions. Plasmid DNA from the binary vector used in the *Agrobacterium* electroporation transformation was included as a control. The PCR reaction was completed using Taq DNA polymerase from Invitrogen (Carlsbad, Calif.) per manufacturer's instructions at 0.5× concentrations. PCR reactions were carried out in a MJ Research Peltier Thermal Cycler programmed with the following conditions: Step 1) 94° C. for 3 minutes; Step 2) 94° C. for 45 seconds; Step 3) 55° C. for 30 seconds; Step 4) 72° C. for 1 minute per kb of expected product length; Step 5) 29 times to Step 2; Step 6) 72° C. for 10 minutes. The reaction was maintained at 4° C. after cycling. The amplification products were analyzed by agarose gel electrophoresis (e.g. 0.7% to 1% agarose, w/v) and visualized by ethidium bromide staining. A colony was selected whose PCR product was identical to the plasmid control.

Example 4

Production of DIG-657. Cells of shake-flask-grown *P. fluorescens* strains harboring expression constructs (pDOW1169) were isolated by centrifugation and the resulting cell pellets frozen at −80° C. Soluble and insoluble fractions from frozen shake flask cell pellet samples were generated using EasyLyse™ Bacterial Protein Extraction Solution (EPICENTRE® Biotechnologies, Madison, Wis.). Each cell pellet was suspended into 1 mL EasyLyse™ solution and further diluted 1:4 in lysis buffer and incubated with shaking at room temperature for 30 minutes. The lysate was centrifuged at 14,000 rpm for 20 minutes at 4° C. and the supernatant was recovered as the soluble fraction. The pellet (insoluble fraction) was then suspended in an equal volume of phosphate buffered saline (PBS; 11.9 mM $Na_2HPO_4$, 137 mM NaCl, 2.7 mM KCl, pH7.4).

Samples were mixed 1:1 with 2× Laemmli sample buffer containing β-mercaptoethanol (Sambrook et al., supra.) and boiled for 5 minutes prior to loading onto Criterion XT® Bis-Tris 12% gels (Bio-Rad Inc., Hercules, Calif.). Electrophoresis was performed in the recommended XT MOPS buffer. Gels were stained with Bio-Safe Coomassie Stain (Bio-Rad, Richmond, Calif.) according to the manufacturer's protocol and imaged using the Alpha Innotech Imaging system (San Leandro, Calif.).

Example 5

Inclusion body preparation. DIG-657 was generally located in the soluble fraction of *P. fluorescens* cells containing the gene for DIG-657. In some cases, a variable percentage of the DIG-657 protein was found located in protein inclusion body (IB) preparations, as demonstrated by SDS-PAGE and MALDI-MS (Matrix Assisted Laser Desorption/Ionization Mass Spectrometry). To isolate this protein from this fraction, *P. fluorescens* fermentation pellets were thawed in a 37° C. water bath. The cells were resuspended to 25% w/v in lysis buffer (50 mM Tris, pH 7.5, 200 mM NaCl, 20 mM EDTA disodium salt (Ethylenediaminetetraacetic acid), 1% Triton X-100, and 5 mM Dithiothreitol (DTT)); 5 mL/L of bacterial protease inhibitor cocktail (P8465 Sigma-Aldrich, St. Louis, Mo.) were added just prior to use. The cells were suspended using a hand-held homogenizer at the lowest setting (Tissue Tearor, BioSpec Products, Inc., Bartlesville, Okla.). Lysozyme (25 mg of Sigma, St. Louis, Mo., L7651 from chicken egg white) was added to the cell suspension by mixing with a metal spatula, and the suspension was incubated at room temperature for one hour. The suspension was cooled on ice for 15 minutes, then sonicated using a Branson (Danbury, Conn.) Sonifier 250 (two 1-minute sessions, at 50% duty cycle, 30% output). Cell lysis was checked by microscopy. An additional 25 mg of lysozyme were added if necessary, and the incubation and sonication steps were repeated. When cell lysis was confirmed via microscopy, the lysate was centrifuged at 11,500×g for 25 minutes (4° C.) to form the IB pellet, and the supernatant was discarded. The IB pellet was resuspended with 100 mL lysis buffer, homogenized with the hand-held mixer and centrifuged as above. The IB pellet was repeatedly washed by resuspension (in 50 mL lysis buffer), homogenization, sonication, and centrifugation until the supernatant became colorless and the IB pellet became firm and off-white in color. For the final wash, the IB pellet was resuspended in sterile-filtered (0.22 µm) distilled water containing 2 mM EDTA, and centrifuged. The final pellet was resuspended in sterile-filtered distilled water containing 2 mM EDTA, and stored in 1 mL aliquots at −80° C.

SDS-PAGE analysis and quantification of protein in IB preparations was done by thawing a 1 mL aliquot of IB pellet and diluting 1:20 with sterile-filtered distilled water. The diluted sample was then boiled with 4× reducing sample buffer [250 mM Tris, pH6.8, 40% glycerol (v/v), 0.4% Bromophenol Blue (w/v), 8% SDS (w/v) and 8% β-Mercapto-ethanol (v/v)] and loaded onto a Novex® 4-20% Tris-Glycine, 12+2 well gel (Invitrogen, Carlsbad, Calif.) run with 1×Tris/Glycine/SDS buffer (BioRad, Richmond, Calif.). The gel was run for 60 min at 200 volts then stained with Coomassie Blue (50% G-250/50% R-250 in 45% methanol, 10% acetic acid), and destained with 7% acetic acid, 5% methanol in distilled water. Quantification of target bands was done by comparing densitometric values for the bands against Bovine Serum Albumin (BSA) samples run on the same gel to generate a standard curve.

Example 6

Solubilization of Inclusion Bodies. Six mL of inclusion body suspension (containing 32 mg/mL of DIG-657 protein) were centrifuged on the highest setting of an Eppendorf model 5415C microfuge (approximately 14,000×g) to pellet the inclusions. The storage buffer supernatant was removed and replaced with 25 mL of 100 mM sodium carbonate buffer, pH11, in a 50 mL conical tube. Inclusions were resuspended using a pipette and vortexed to mix thoroughly. The tube was placed on a gently rocking platform at 4° C. overnight to extract the target protein. The extract was centrifuged at 30,000×g for 30 min at 4° C., and the resulting supernatant was concentrated 5-fold using an Amicon Ultra-15 regenerated cellulose centrifugal filter device (30,000 Molecular Weight Cutoff; Millipore, Billerica, Mass.). The sample buffer was then changed to 10 mM CAPS [3-(cyclohexamino)1-propanesulfonic acid] pH 10, using disposable PD-10 columns (GE Healthcare, Piscataway, N.J.).

Example 7

Gel electrophoresis. The concentrated extract was prepared for electrophoresis by diluting 1:50 in NuPAGE® LDS sample buffer (Invitrogen, Carlsbad, Calif.) containing κ mM dithiothreitol as a reducing agent and heated at 95° C. for 4 minutes. The sample was loaded in duplicate lanes of a 4-12% NuPAGE® gel alongside five BSA standards ranging from 0.2 to 2 µg/lane (for standard curve generation). Voltage was applied at 200V using MOPS SDS running buffer (Invitrogen, Carlsbad, Calif.) until the tracking dye reached the bottom of the gel. The gel was stained with 0.2% Coomassie Blue G-250 in 45% methanol, 10% acetic acid, and destained, first briefly with 45% methanol, 10% acetic acid, and then at length with 7% acetic acid, 5% methanol until the background cleared. Following destaining, the gel was scanned with a Biorad Fluor-S Multilmager. The instrument's Quantity One v.4.5.2 Software was used to obtain background-subtracted volumes of the stained protein bands and to generate the BSA standard curve that was used to calculate the concentration of DIG-657 protein in the stock solution.

Example 8

DIG-657 purification. Purification of DIG-657 was conducted similar to VIP3 as described by Lee, M. K., et al (2003), where cells from Pf transformed with the DIG-657 gene were defrosted, suspended into extraction buffer (10 mM Tris-HCl, 2 mM EDTA, 2 mM DTT) in the presence of 0.5 ml protease inhibitor cocktail (Sigma, St. Louis, Mo.) and sonicated five times for one min. each, with resting on ice for 1 min. between each sonication cycle. The solution was centrifuged at 20,000×g for 10 min., and the supernatant collected and applied to a MonoQ ion exchange column (1 cm dia.×10 cm long). Protein purification was achieved by sequential chromatography on ion exchange (MonoQ 1010, GE Healthcare, Piscataway, N.J.), hydrophobic chromatography, and size exclusion chromatography. The final preparation showed a single band of protein migrating at an apparent molecular weight of about 90 kDa.

Example 9

Sample preparation and bioassays. Purified preparations of DIG-657 were diluted appropriately in 10 mM CAPS, pH 10, and all bioassays contained a control treatment consisting of this buffer, which served as a background check for mortality and/or growth inhibition. Protein concentrations in bioassay buffer were estimated by gel electrophoresis using bovine serum albumin (BSA) to create a standard curve for gel densitometry, which was measured using a BioRad (Richmond, Calif.) imaging system (Fluor-S MultiImager with Quantity One software version 4.5.2). Proteins in the gel matrix were stained with Coomassie Blue-based stain and destained before reading.

Purified proteins were tested for insecticidal activity in bioassays conducted with 1-2 day old neonate Lepidopteran larvae on artificial insect diet. Larvae of CEW, SBL, DBM, VBC, ECB, FAW and TBW were hatched from eggs obtained from a colony maintained by a commercial insectary (Benzon Research Inc., Carlisle, Pa.). Larvae of rECB and rFAW were hatched from eggs harvested from proprietary colonies (Dow AgroSciences LLC, Indianapolis, Ind.).

The bioassays were conducted in 128-well plastic trays specifically designed for insect bioassays (C-D International, Pitman, N.J.). Each well contained 2.0 mL of Multi-species Lepidoptera diet (Southland Products, Lake Village, Ark.). A 40 μL aliquot of protein sample was delivered by pipette onto the 2.0 $cm^2$ diet surface of each well (20 $\mu L/cm^2$). Diet concentrations were calculated as the amount (ng) of DIG-657 protein per square centimeter (cm$^2$) of surface area in the well. A 9 dose concentration range was used from 9,000 to 3 ng/cm$^2$ with 16 larvae tested per dose. The treated trays were held in a fume hood until the liquid on the diet surface had evaporated or was absorbed into the diet.

Within a 24-48 hours of eclosion, individual larvae were picked up with a moistened camel hair brush and deposited on the treated diet, one larva per well. The infested wells were then sealed with adhesive sheets of clear plastic and vented to allow gas exchange (C-D International, Pitman, N.J.). Bioassay trays were held under controlled environmental conditions (28° C., ~60% Relative Humidity, 16:8 [Light:Dark]) for 5 days, after which the total number of insects exposed to each protein sample, the number of dead insects, and the weight of surviving insects were recorded. Percent mortality and percent growth inhibition were calculated for each treatment. Growth inhibition (GI) was calculated using the formula below:

$$GI = [1-(TWIT/TNIT)/(TWIBC/TNIBC)]$$

where TWIT is the Total Weight of Insects in the Treatment, TNIT is the Total Number of Insects in the Treatment, TWIBC is the Total Weight of Insects in the Background Check (Buffer control), and TNIBC is the Total Number of Insects in the Background Check (Buffer control).

The GI$_{50}$ was determined to be the concentration of DIG-657 protein in the diet at which the GI value was 50%. The 50% lethal concentration (LC50) was recorded as the concentration of DIG-657 protein in the diet at which 50% of test insects were killed. Growth inhibition concentration-response curves were determined by using a nonlinear logistic 3-parameter through JMP Pro, version 9.0.3, software (SAS Institute Inc., Cary, N.C.). Lethal concentration-response curve were analyzed by Probit analyses (Finney, 1971) of the pooled mortality data and were conducted using POLO-PC (LeOra Software).

Table 2 presents the results of bioassay tests of DIG-657 protein on ECB, rECB, TBW, *Pseudoplusia includens* (Walker) (soybean looper, "SBL"), *Anticarsia gemmatalis* (Hubner) (velvetbean caterpillar, "VBC"), CEW, FAW, rFAW, and DBM. An unexpected and surprising finding is that the rECB test insects were as susceptible if not more to the action of DIG-657 protein as were the susceptible strain of ECB insects.

TABLE 2

Efficacy of purified DIG-657 against multiple insect species tested on artificial diet-overlay bioassay (ng/cm$^2$).

| Insect | LC$_{50}$ (CI 95%)(ng/cm$^2$) | GI$_{50}$ (CI 95%)(ng/cm$^2$) |
|---|---|---|
| ECB | 281 (166-470) | 8.6 (6.6-11.1) |
| rECB | 37 (17-74) | 8.1 (4.2-15.9) |

TABLE 2-continued

Efficacy of purified DIG-657 against multiple insect species tested on artificial diet-overlay bioassay (ng/cm$^2$).

| Insect | LC$_{50}$ (CI 95%)(ng/cm$^2$) | GI$_{50}$ (CI 95%)(ng/cm$^2$) |
|---|---|---|
| TBW | 608 (311-1,432) | 12.9 (5.9-28.1) |
| SBL | 80 (50-120) | 5.4 (4.3-6.7) |
| VBC | 66 (45-95) | 18.9 (12.2-29.3) |
| CEW | >9,000 | 17.5 (10.9-28.2) |
| FAW | >9,000 | 563 (398-796) |
| rFAW | ~9,000 | 2,651 (1,030-6,822) |
| DBM | 6.3 (1.6-11.8) | 3.7 (3.0-4.6) |

*Helicoverpa armigera* bioassays were conducted by surface contamination, using neonate larvae. Toxicity tests were performed in 128-cell trays, each cell 2 cm$^2$. Concentrations of 25 and 2500 ng/cm$^2$ were used to determine percent mortality, with a control of buffer only (Table3). Tests to determine LC$_{50}$ values were performed using 7 different concentrations of purified protoxins, with a control of only buffer (Table 4). Mortality and arrest were assessed after 7 days at 25° C. with 16:8 light:dark conditions. "Functional mortality" was obtained scoring dead and L1 arrested larvae. Results showed DIG-657 activity against *Helicoverpa armigera*.

TABLE 3

Percent mortality of DIG-657 against *Helicoverpa armigera* tested on artificial diet bioassay.

| | Mortality % | | Functional Mortality % | |
|---|---|---|---|---|
| | 25 ng/cm$^2$ | 2500 ng/cm$^2$ | 25 ng/cm$^2$ | 2500 ng/cm$^2$ |
| Cry1Ac | 28 | 92 | 33 | 100 |
| Cry1Fa | 6 | 21 | 6 | 21 |
| DIG-657 | 38 | 79 | 38 | 93 |

TABLE 4

LC$_{50}$ (ng/cm$^2$) of DIG-657 against *Helicoverpa armigera* tested on artificial diet bioassay.

| | | Mortality | | Functional Mortality | |
|---|---|---|---|---|---|
| Toxin | Reps | LC$_{50}$* | Slope | LC$_{50}$* | Slope |
| Cry1Ac | 3 | 13.6 (0.3-44.9) | 0.65 ± 0.12 | 5.05 (0.02-19.27) | 0.87 ± 0.16 |
| DIG-657 | 5 | 3389 (963-79246) | 0.56 ± 0.08 | 301 (183-541) | 0.84 ± 0.08 |

*Values in ( ) are 0.95 confidence limits

Example 10

Production of DIG-657 Bt Insecticidal Proteins and Variants in Dicot Plants

*Arabidopsis* Transformation.

*Arabidopsis thaliana* Col-01 is transformed using the floral dip method (Weigel and Glazebrook, 2002). The selected *Agrobacterium* colony is used to inoculate 1 mL to 15 mL cultures of YEP broth containing appropriate antibiotics for selection. The culture is incubated overnight at 28° C. with constant agitation at 220 rpm. Each culture is used to inoculate two 500 mL cultures of YEP broth containing appropriate antibiotics for selection and the new cultures are incubated overnight at 28° C. with constant agitation. The cells are pelleted at approximately 8700×g for 10 minutes at room temperature, and the resulting supernatant is discarded. The cell pellet is gently resuspended in 500 mL of infiltration media containing: ½× Murashige and Skoog salts (Sigma-Aldrich)/Gamborg's B5 vitamins (Gold Bio-Technology, St. Louis, Mo.), 10% (w/v) sucrose, 0.044 µM benzylaminopurine (10 µL/L of 1 mg/mL stock in DMSO) and 300 µL/L Silwet L-77. Plants approximately 1 month old are dipped into the media for 15 seconds, with care taken to assure submergence of the newest inflorescence. The plants are then laid on their sides and covered (transparent or opaque) for 24 hours, washed with water, and placed upright. The plants are grown at 22° C., with a 16:8 light:dark photoperiod. Approximately 4 weeks after dipping, the seeds are harvested.

Arabidopsis Growth and Selection.

Freshly harvested T1 seed is allowed to dry for at least 7 days at room temperature in the presence of desiccant. Seed is suspended in a 0.1% agar/water (Sigma-Aldrich) solution and then stratified at 4° C. for 2 days. To prepare for planting, Sunshine Mix LP5 (Sun Gro Horticulture Inc., Bellevue, Wash.) in 10.5 inch×21 inch germination trays (T.O. Plastics Inc., Clearwater, Minn.) is covered with fine vermiculite, sub-irrigated with Hoagland's solution (Hoagland and Arnon, 1950) until wet, then allowed to drain for 24 hours. Stratified seed is sown onto the vermiculite and covered with humidity domes (KORD Products, Bramalea, Ontario, Canada) for 7 days. Seeds are germinated and plants are grown in a Conviron (Models CMP4030 or CMP3244; Controlled Environments Limited, Winnipeg, Manitoba, Canada) under long day conditions (16:8 light: dark photoperiod) at a light intensity of 120-150 mol/m$^2$sec under constant temperature (22° C.) and humidity (40-50%). Plants are initially watered with Hoagland's solution and subsequently with deionized water to keep the soil moist but not wet.

The domes are removed 5-6 days post sowing and plants are sprayed with a chemical selection agent to kill plants germinated from nontransformed seeds. For example, if the plant expressible selectable marker gene provided by the binary plant transformation vector is a pat or bar gene (Wehrmann et al., 1996), transformed plants may be selected by spraying with a 1000× solution of Finale (5.78% glufosinate ammonium, Farnam Companies Inc., Phoenix, Ariz.). Two subsequent sprays are performed at 5-7 day intervals. Survivors (plants actively growing) are identified 7-10 days after the final spraying and are transplanted into pots prepared with Sunshine Mix LP5. Transplanted plants are covered with a humidity dome for 3-4 days and placed in a Conviron under the above-mentioned growth conditions.

Those skilled in the art of dicot plant transformation will understand that other methods of selection of transformed plants are available when other plant expressible selectable marker genes (e.g. herbicide tolerance genes) are used.

Example 11

Transgenic *Glycine max* Comprising DIG-657.

Ten to 20 transgenic T$_0$ *Glycine max* plants harboring expression vectors for nucleic acids comprising DIG-657 are generated as is known in the art, including for example by *Agrobacterium*-mediated transformation. Mature soybean (*Glycine max*) seeds are sterilized overnight with chlorine gas for sixteen hours. Following sterilization with chlorine gas, the seeds are placed in an open container in a LAMINAR™ flow hood to dispel the chlorine gas. Next, the sterilized seeds are imbibed with sterile H$_2$O for sixteen hours in the dark using a black box at 24° C.

Preparation of split-seed soybeans. The split soybean seed comprising a portion of an embryonic axis protocol requires preparation of soybean seed material which is cut longitudinally, using a #10 blade affixed to a scalpel, along the hilum of the seed to separate and remove the seed coat, and to split the seed into two cotyledon sections. Careful attention is made to partially remove the embryonic axis, wherein about ½-⅓ of the embryo axis remains attached to the nodal end of the cotyledon.

Inoculation. The split soybean seeds comprising a partial portion of the embryonic axis are then immersed for about 30 minutes in a solution of *Agrobacterium tumefaciens* (e.g., strain EHA 101 or EHA 105) containing binary plasmid comprising DIG-657. The *Agrobacterium tumefaciens* solution is diluted to a final concentration of λ=0.6 OD$_{650}$ before immersing the cotyledons comprising the embryo axis.

Co-cultivation. Following inoculation, the split soybean seed is allowed to co-cultivate with the *Agrobacterium tumefaciens* strain for 5 days on co-cultivation medium (Wang, Kan. *Agrobacterium Protocols*. 2. 1. New Jersey: Humana Press, 2006. Print.) in a Petri dish covered with a piece of filter paper.

Shoot induction. After 5 days of co-cultivation, the split soybean seeds are washed in liquid Shoot Induction (SI) media consisting of B5 salts, B5 vitamins, 28 mg/L Ferrous, 38 mg/L Na$_2$EDTA, 30 g/L sucrose, 0.6 g/L MES, 1.11 mg/L BAP, 100 mg/L TIMENTIN™, 200 mg/L cefotaxime, and 50 mg/L vancomycin (pH 5.7). The split soybean seeds are then cultured on Shoot Induction I (SI I) medium consisting of B5 salts, B5 vitamins, 7 g/L Noble agar, 28 mg/L Ferrous, 38 mg/L Na$_2$EDTA, 30 g/L sucrose, 0.6 g/L MES, 1.11 mg/L BAP, 50 mg/L TIMENTIN™, 200 mg/L cefotaxime, 50 mg/L vancomycin (pH 5.7), with the flat side of the cotyledon facing up and the nodal end of the cotyledon imbedded into the medium. After 2 weeks of culture, the explants from the transformed split soybean seed are transferred to the Shoot Induction II (SI II) medium containing SI I medium supplemented with 6 mg/L glufosinate (LIBERTY®).

Shoot elongation. After 2 weeks of culture on SI II medium, the cotyledons are removed from the explants and a flush shoot pad containing the embryonic axis are excised by making a cut at the base of the cotyledon. The isolated shoot pad from the cotyledon is transferred to Shoot Elongation (SE) medium. The SE medium consists of MS salts, 28 mg/L Ferrous, 38 mg/L Na$_2$EDTA, 30 g/L sucrose and 0.6 g/L MES, 50 mg/L asparagine, 100 mg/L L-pyroglutamic acid, 0.1 mg/L IAA, 0.5 mg/L GA3, 1 mg/L zeatin riboside, 50 mg/L TIMENTIN™, 200 mg/L cefotaxime, 50 mg/L vancomycin, 6 mg/L glufosinate, 7 g/L Noble agar, (pH 5.7). The cultures are transferred to fresh SE medium every 2 weeks. The cultures are grown in a CONVIRON™ growth chamber at 24° C. with an 18 h photoperiod at a light intensity of 80-90 mol/m$^2$sec.

Rooting. Elongated shoots which developed from the cotyledon shoot pad are isolated by cutting the elongated shoot at the base of the cotyledon shoot pad, and dipping the elongated shoot in 1 mg/L IBA (Indole 3-butyric acid) for 1-3 minutes to promote rooting. Next, the elongated shoots are transferred to rooting medium (MS salts, B5 vitamins, 28 mg/L Ferrous, 38 mg/L Na$_2$EDTA, 20 g/L sucrose and 0.59 g/L MES, 50 mg/L asparagine, 100 mg/L L-pyroglutamic acid 7 g/L Noble agar, pH 5.6) in phyta trays.

Cultivation. Following culture in a CONVIRON™ growth chamber at 24° C., 18 h photoperiod, for 1-2 weeks, the shoots which have developed roots are transferred to a soil mix in a covered sundae cup and placed in a CONVIRON™ growth chamber (models CMP4030 and CMP3244, Controlled Environments Limited, Winnipeg, Manitoba, Canada) under long day conditions (16 hours light/8 hours dark) at a light intensity of 120-150 µmol/m²sec under constant temperature (22° C.) and humidity (40-50%) for acclimatization of plantlets. The rooted plantlets are acclimated in sundae cups for several weeks before they are transferred to the greenhouse for further acclimatization and establishment of robust transgenic soybean plants.

Development and morphological characteristics of transgenic lines are compared with nontransformed plants. Plant root, shoot, foliage and reproduction characteristics are compared. There are no observable difference in root length and growth patterns of transgenic and nontransformed plants. Plant shoot characteristics such as height, leaf numbers and sizes, time of flowering, floral size and appearance are similar. In general, there are no observable morphological differences between transgenic lines and those without expression of DIG proteins when cultured in vitro and in soil in the glasshouse.

Example 12

Production of DIG-657 Bt Insecticidal Proteins and Variants in Monocot Plants

*Agrobacterium*-Mediated Transformation of Maize.

Seeds from a High II or B-104 $F_1$ cross (Armstrong et al., 1991) were planted into 5-gallon-pots containing a mixture of 95% Metro-Mix 360 soilless growing medium (Sun Gro Horticulture, Bellevue, Wash.) and 5% clay/loam soil. The plants were grown in a greenhouse using a combination of high pressure sodium and metal halide lamps with a 16:8 hour light:dark photoperiod. To obtain immature F2 embryos for transformation, controlled sib-pollinations were performed. Immature embryos were isolated at 8-10 days post-pollination when embryos were approximately 1.0 to 2.0 mm in size.

Infection and co-cultivation Maize ears were surface sterilized by scrubbing with liquid soap, immersing in 70% ethanol for 2 minutes, and then immersing in 20% commercial bleach (0.1% sodium hypochlorite) for 30 minutes before being rinsed with sterile water.

A suspension of *Agrobacterium* cells containing a superbinary vector were prepared by transferring 1-2 loops of bacteria grown on YEP solid medium containing 100 mg/L spectinomycin, 10 mg/L tetracycline, and 250 mg/L streptomycin at 28° C. for 2-3 days into 5 mL of liquid infection medium (LS Basal Medium (Linsmaier and Skoog, 1965), N6 vitamins (Chu et al., 1975), 1.5 mg/L 2,4-Dichlorophenoxyacetic acid (2,4-D), 68.5 gm/L sucrose, 36.0 gm/L glucose, 6 mM L-proline, pH 5.2) containing 100 μM acetosyringone. The solution was vortexed until a uniform suspension was achieved, and the concentration was adjusted to a final density of about 200 Klett units, using a Klett-Summerson colorimeter with a purple filter, or an optical density of approximately 0.4 at 550 nm. Immature embryos were isolated directly into a micro centrifuge tube containing 2 mL of the infection medium. The medium was removed and replaced with 1 mL of the *Agrobacterium* solution with a density of 200 Klett units, and the *Agrobacterium* and embryo solution was incubated for 5 minutes at room temperature and then transferred to co-cultivation medium (LS Basal Medium, (containing N6 vitamins, 1.5 mg/L 2,4-D, 30.0 gm/L sucrose, 6 mM L-proline, 0.85 mg/L $AgNO_3$, 100 μM acetosyringone, and 3.0 gm/L Gellan gum (PhytoTechnology Laboratories, Lenexa, Kans.), pH 5.8) for 5 days at 25° C. under dark conditions.

After co-cultivation, the embryos were transferred to selective medium after which transformed isolates were obtained over the course of approximately 8 weeks. For selection of maize tissues transformed with a superbinary plasmid containing a plant expressible pat or bar selectable marker gene, an LS based medium (LS Basal medium, with 1×N6 vitamins, 1.5 mg/L 2,4-D, 0.5 gm/L MES (2-(N-morpholino)ethanesulfonic acid monohydrate; PhytoTechnology Laboratories., Lenexa, Kans.), 30.0 gm/L sucrose, 6 mM L-proline, 1.0 mg/L $AgNO_3$, 250 mg/L cefotaxime, 2.5 gm/L Gellan gum, pH 5.7) was used with Bialaphos (Gold BioTechnology, St. Louis, Mo.). The embryos were transferred to selection media containing 3 mg/L Bialaphos until embryogenic isolates were obtained. Recovered isolates were bulked up by transferring to fresh selection medium at 2-week intervals for regeneration and further analysis. Those skilled in the art of maize transformation will understand that other methods of selection of transformed plants are available when other plant expressible selectable marker genes (e.g. herbicide tolerance genes) are used.

Two different constructs of DIG-657 contained in plasmids pDAB114534 and pDAB114535 (SEQ ID NO:5 and SEQ ID NO:6) (Table 5) were transformed into maize. T0 plants were regenerated and tested for their ability to control target insect pests. Construct pDAB115782 is a plasmid containing the gene for a YFP (yellow fluorescent protein) used as a negative control for a plant transformed with a non-insecticidal gene.

TABLE 5

Description of Plasmids containing different DIG-657 constructs transformed into maize plants.

| Plasmid: | Description: | Feature: |
|---|---|---|
| pDAB114534 | BorderB::ZmUbi1/IRDIG9931.4/ ZmPer5::ZCZ018::SCBV(MAM)/ AAD-1/ZmLip::3x Border A | DIG-657 full length (SEQ ID NO: 5) |
| pDAB114535 | BorderB::ZmUbi1/IRDIG9931.5/ ZmPer5::ZCZ018::SCBV(MAM)/ AAD-1/ZmLip::3x Border A | DIG-657 Truncated (SEQ ID NO: 6) |
| pDAB115782 | BorderB::ZmUbi1/PhiYFPv3/ ZmPer5::ZCZ018::SCBV(MAM)/ AAD-1/ZmLip::3x Border A | PhiYFP |

A 1.0×0.5 inch square leaf cutting was taken in duplicate from the V3 or V4 leaf of V5 To transgenic plants. For each test, wild type plant leaf tissues were sampled first to prevent cross contamination of Bt toxins on the leaf edges, followed by the transformed plants. In each bioassay tray well (32-well trays and lids, CD International, Pitman, N.J.), 1 leaf cutting was placed on 2% water-agar (Fisher Scientific, Fair Lawn, N.J.) and this was replicated 2 times per insect species, per event and per construct. Each well was infested with ten ECB or *Diatraea saccharalis* (Fabricius) (Sugarcane Borer "SCB") neonates (24-48 hrs old) and sealed with a plastic perforated lid to allow for air exchange. The trays were placed at 28° C. (16:8 hr light:dark, 40% RH) and after 3 days they were graded for percent leaf damage. The percent leaf damage data was analyzed with ANOVA and mean separations with the Tukey-Kramer test when variances were homogenous by using JMP® Pro 9.0.1 (2010 SAS Institute Inc., Cary, N.C.). The level of leaf damage observed by each insect species on transgenic plant material is shown in Table 6.

TABLE 6

Mean percent leaf damage caused by ECB or SCB larvae feeding on T₀ maize leaf tissues from constructs 114534, 114535 or 115782

| Construct | Average % Leaf Damage by ECB | Std. Dev. | Average % Leaf Damage by SCB | Std. Dev. |
|---|---|---|---|---|
| pDAB114534 (FL DIG-657) | 14.4 | 15.3 | 8.7 | 2.9 |
| pDAB114535 (Tr DIG-657) | 71.8 | 26.9 | 93.3 | 9.3 |
| 115782 (YFP) | 90.8 | 8.5 | 98.8 | 3.1 |

* standard deviation (n = 10)

Both constructs 114534 and 114535 resulted in less mean damage as compared to the YFP negative control construct (115782). Construct 114534 expressing the full length DIG-657 protein exhibited greater insect activity over construct 114535 expressing the truncated DIG-657 protein.

Example 13

Regeneration and seed production.

For regeneration, the cultures were transferred to "28" induction medium (MS salts and vitamins, 30 gm/L sucrose, 5 mg/L Benzylaminopurine, 0.25 mg/L 2, 4-D, 3 mg/L Bialaphos, 250 mg/L cefotaxime, 2.5 gm/L Gellan gum, pH 5.7) for 1 week under low-light conditions (14 µEm$^{-2}$s$^{-1}$) then 1 week under high-light conditions (approximately 89 µEm$^{-2}$s$^{-1}$). Tissues were subsequently transferred to "36" regeneration medium (same as induction medium except lacking plant growth regulators). Plantlets 3-5 cm in length were transferred to glass culture tubes containing SHGA medium (Schenk and Hildebrandt salts and vitamins (1972); PhytoTechnology Laboratories., Lenexa, Kans.), 1.0 gm/L myo-inositol, 10 gm/L sucrose and 2.0 gm/L Gellan gum, pH 5.8) to allow for further growth and development of the shoot and roots. Plants were transplanted to the same soil mixture as described earlier herein and grown to flowering in the greenhouse. Controlled pollinations for seed production were conducted.

Example 14

Design of a Plant-Optimized Version of the Coding Sequence for the DIG-657 Bt Insecticidal Protein.

A DNA sequence having a plant codon bias was designed and synthesized to produce the DIG-657 protein in transgenic monocot and dicot plants. A codon usage table for maize (*Zea mays* L.) was calculated from 706 protein coding sequences (CDs) obtained from sequences deposited in GenBank. Codon usage tables for tobacco (*Nicotiana tabacum,* 1268 CDs), canola (*Brassica napus,* 530 CDs), cotton (*Gossypium hirsutum,* 197 CDs), and soybean (*Glycine max*; ca. 1000 CDs) were downloaded from data at the website http://www kazusa.or.jp/codon/. A biased codon set that comprises highly used codons common to both maize and dicot datasets, in appropriate weighted average relative amounts, was calculated after omitting any redundant codon used less than about 10% of total codon uses for that amino acid in either plant type. To derive a plant optimized sequence encoding the DIG-657 protein, codon substitutions to the experimentally determined DIG-657 DNA sequence were made such that the resulting DNA sequence had the overall codon composition of the plant-optimized codon bias table. Further refinements of the sequence were made to eliminate undesirable restriction enzyme recognition sites, potential plant intron splice sites, long runs of A/T or C/G residues, and other motifs that might interfere with RNA stability, transcription, or translation of the coding region in plant cells. Other changes were made to introduce desired restriction enzyme recognition sites, and to eliminate long internal Open Reading Frames (frames other than +1). These changes were all made within the constraints of retaining the plant-biased codon composition. Synthesis of the designed sequence was performed by a commercial vendor (DNA2.0, Menlo Park, Calif.). Additional guidance regarding the production of synthetic genes can be found in, for example, WO 97/13402 and U.S. Pat. No. 5,380,831. A maize-optimized DNA sequence encoding DIG-657 variant1 is given in SEQ ID NO:3. A *Pseudomonas fluorescens* optimized DNA sequence encoding DIG-657 variant2 is given in SEQ ID NO:4. A maize-optimized high GC DNA sequence encoding DIG-657 is given in SEQ ID NO:5. A maize-optimized high GC DNA sequence encoding DIG-657 gene truncated 204 aa from the N-terminal is given in SEQ ID NO:6. A dicot-optimized DNA sequence encoding the full length DIG-657 is disclosed as SEQ ID NO:8. A dicot-optimized DNA sequence encoding the truncated DIG-657 is disclosed as SEQ ID NO:9.

Hybridization of immobilized DNA on Southern blots with radioactively labeled gene-specific probes is performed by standard methods Sambrook et al., supra.). Radioactive isotopes used for labeling polynucleotide probes include 32P, 33P, 14C, or 3H. Incorporation of radioactive isotopes into polynucleotide probe molecules is done by any of several methods well known to those skilled in the field of molecular biology. (See, e.g. Sambrook et al., supra.) In general, hybridization and subsequent washes are carried out under stringent conditions that allow for detection of target sequences with homology to the claimed toxin encoding genes. For double-stranded DNA gene probes, hybridization is carried out overnight at 20° C. to 25° C. below the $T_m$ of the DNA hybrid in 6×SSPE, 5×Denhardt's Solution, 0.1% SDS, 0.1 mg/mL denatured DNA [20×SSPE is 3M NaCl, 0.2 M $NaHPO_4$, and 0.02M EDTA (ethylenediamine tetra-acetic acid sodium salt); 100×Denhardt's Solution (20 gm/L Polyvinylpyrollidone, 20 gm/L Ficoll type 400 and 20 gm/L BSA-fraction V).

Washes are typically be carried out as follows:

a. Twice at room temperature for 15 minutes in 1×SSPE, 0.1% SDS (low stringency wash).

b. Once at 20° C. below the $T_m$ temperature for 15 minutes in 0.2×SSPE, 0.1% SDS (moderate stringency wash).

For oligonucleotide probes, hybridization may be carried out overnight at 10° C. to 20° C. below the $T_m$ of the hybrid in 6×SSPE, 5×Denhardt's solution, 0.1% SDS, 0.1 mg/mL denatured DNA. $T_m$ for oligonucleotide probes may be determined by the following formula (Suggs et al., 1981).

$$T_m(° C.)=2(\text{number of } T/A \text{base pairs})+4(\text{number of } G/C \text{base pairs})$$

Washes are typically be carried out as follows:

a. Twice at room temperature for 15 minutes 1×SSPE, 0.1% SDS (low stringency wash).

b. Once at the hybridization temperature for 15 minutes in 1×SSPE, 0.1% SDS (moderate stringency wash).

Probe molecules for hybridization and hybrid molecules formed between probe and target molecules may be rendered detectable by means other than radioactive labeling. Such alternate methods are intended to be within the scope of this invention.

While the present disclosure may be susceptible to various modifications and alternative forms, specific embodiments have been described by way of example in detail herein. However, it should be understood that the present disclosure is not intended to be limited to the particular forms disclosed. Rather, the present disclosure is to cover all modifications, equivalents, and alternatives falling within the scope of the present disclosure as defined by the following appended claims and their legal equivalents.

What is claimed is:

1. A nucleic acid construct comprising one or more heterologous regulatory sequences that drives expression of the nucleic acid sequence of SEQ ID NO:9.

2. A plant, seed, or plant part comprising the nucleic acid construct of claim 1.

3. The plant or plant part of claim 2, wherein the polypeptide encoded by the nucleic acid construct has insecticidal activity against an insect selected from the group consisting of European Corn Borer, Cry1F resistant European Corn Borer, Soybean Looper, Velvetbean Caterpillar, Tobacco Budworm, Cotton Bollworm, Corn Earworm, and Diamondback Moth.

4. A method for producing an insect resistant plant variety comprising breeding a non-transgenic plant with the transgenic plant of claim 2 and selecting progeny by analyzing for at least a portion of the foreign DNA construct from said insect resistant plant.

* * * * *